(12) United States Patent
Kardon et al.

(10) Patent No.: US 7,118,217 B2
(45) Date of Patent: Oct. 10, 2006

(54) DEVICE AND METHOD FOR OPTICAL IMAGING OF RETINAL FUNCTION

(75) Inventors: Randy H. Kardon, Iowa City, IA (US); Young H. Kwon, Iowa City, IA (US); Daniel Tso, Jamesville, NY (US); Peter Soliz, Albuquerque, NM (US)

(73) Assignees: University of Iowa Research Foundation, Iowa City, IA (US); The Research Foundation of State Univ. of New York, Albany, NY (US); Kestrel Corporation, Albuquerque, NM (US)

( * ) Notice: Subject to any disclaimer, the term of this patent is extended or adjusted under 35 U.S.C. 154(b) by 124 days.

(21) Appl. No.: 10/347,142

(22) Filed: Jan. 17, 2003

(65) Prior Publication Data

US 2004/0075812 A1    Apr. 22, 2004

Related U.S. Application Data

(60) Provisional application No. 60/349,435, filed on Jan. 18, 2002.

(51) Int. Cl.
*A61B 3/14* (2006.01)
*A61B 3/10* (2006.01)

(52) U.S. Cl. .................. 351/206; 351/206; 351/221; 600/473; 600/476

(58) Field of Classification Search ............ 351/205, 351/206, 211, 213, 221, 246; 600/473, 476, 600/317, 558
See application file for complete search history.

(56) References Cited

U.S. PATENT DOCUMENTS

| | | | | |
|---|---|---|---|---|
| 3,954,329 A | * | 5/1976 | Pomerantzeff | 351/221 |
| 4,200,362 A | * | 4/1980 | Pomerantzeff | 351/221 |
| 4,305,398 A | | 12/1981 | Sawa | 128/633 |
| 4,569,354 A | | 2/1986 | Shapiro et al. | 128/665 |
| 4,922,919 A | | 5/1990 | Novack | 128/633 |
| 5,215,095 A | | 6/1993 | Macvicar et al. | 128/665 |
| 5,219,400 A | | 6/1993 | Jacot et al. | 128/633 |
| 5,400,791 A | | 3/1995 | Schlier et al. | 128/664 |

(Continued)

FOREIGN PATENT DOCUMENTS

WO    WO 00/06015    2/2000

OTHER PUBLICATIONS

PCT International Search Report Application No. PCT/US 03/03191.

(Continued)

*Primary Examiner*—Charles A Marmor, II
*Assistant Examiner*—John R Sanders
(74) *Attorney, Agent, or Firm*—Needle & Rosenberg, PC

(57) ABSTRACT

An Optical Imaging Device of Retinal Function has been developed to detect changes in reflectance of near infrared light from the retina of human subjects in response to visual activation of the retina by a pattern stimulus. The measured changes in reflectance correspond in time to the onset and offset of the visual stimulus in the portion of the retina being stimulated. Any changes in reflectance can be measured by interrogating the retina with a light source. The light source may be presented to the retina via the cornea and pupil or through other tissues in and around the eye. Different wavelengths of interrogating light may be used to interrogate various layers of the retina. Additionally, various novel patterns and methods of stimulation have been developed for use with the imaging device and methods.

44 Claims, 21 Drawing Sheets

U.S. PATENT DOCUMENTS

| | | | |
|---|---|---|---|
| 5,485,229 A | 1/1996 | Hare | 351/215 |
| 5,626,134 A | 5/1997 | Zuckerman | 128/633 |
| 5,853,370 A | 12/1998 | Chance et al. | 600/473 |
| 5,966,196 A * | 10/1999 | Svetliza et al. | 351/205 |
| 6,161,031 A | 12/2000 | Hochman et al. | 600/407 |
| 6,233,480 B1 | 5/2001 | Hochman et al. | 600/476 |
| 6,478,424 B1 * | 11/2002 | Grinvald et al. | 351/206 |
| 2001/0056247 A1 | 12/2001 | Faubert et al. | |
| 2004/0156016 A1 * | 8/2004 | Kerr et al. | 351/206 |

OTHER PUBLICATIONS

European Patent Application No. 0 686 372 A1.

* cited by examiner

| column\row | 2 | 3 | 4 | 5 | 6 | 7 | 8 |
|---|---|---|---|---|---|---|---|
| 2 |  |  |  |  |  |  |  |
| 3 | 0.84 | 0.68 | 0.92 | 0.89 | 0.91 | 0.95 | 0.91 |
| 4 | 0.94 | 0.95 | 0.97 | 0.99 | 0.98 | 0.96 | 0.92 |
| 5 | 0.89 | 0.97 | 0.99 | 1.00 | 0.97 | 0.93 | 0.92 |
| 6 | 0.79 | 0.94 | 0.95 | 0.89 | 0.68 | 0.50 | 0.45 |
| 7 | 0.54 | 0.78 | 0.80 | 0.81 | 0.59 | 0.18 | 0.57 |
| 8 | 0.83 | 0.42 | 0.02 | 0.04 | 0.10 | 0.21 | 0.08 |
| 9 |  | 0.52 | 0.65 | 0.38 | 0.31 | 0.29 | 0.35 |
|  |  | 0.88 | 0.46 | 0.46 | 0.27 | 0.19 | 0.22 |

Fig. 8

DEVICE AND METHOD FOR OPTICAL IMAGING OF RETINAL FUNCTION

CROSS-REFERENCE TO RELATED APPLICATION

The benefit of the filing date of U.S. Provisional Patent Application Ser. No. 60/349,435, filed Jan. 18, 2002, entitled "OPTICAL IMAGING DEVICE OF RETINA FUNCTION," is hereby claimed, and the specification thereof incorporated herein in its entirety.

ACKNOWLEDGMENT

This invention was made with government support under Grant number 1R43EY12915-01A1 awarded by the National Eye Institute. The government has certain rights in the invention.

FIELD OF THE INVENTION

The invention relates in general to retinal neuronal activity imaging. More particularly, the invention relates to instrumentation and methodologies in the diagnostic imaging of stimulus responsive ocular fundus neuronal activity.

BACKGROUND OF THE INVENTION

The current standard for detecting and monitoring progression of diseases of the optic nerve (i.e. glaucoma, ischemic optic neuropathy, compressive optic neuropathy) and retina is visual field testing (perimetry). Perimetry is a functional test of the patient's vision. The shape and extent of the defect on the visual field map allows the clinician to confirm the presence of damage, helps to determine damage location along the visual pathway (retina, optic nerve, chiasm, optic tract, postgeniculate fibers), and is essential in monitoring progression or improvement over time.

Perimetry remains a subjective test that requires the patient to make important judgments and reports during the test that can be clouded by anxiety, fatigue, or lack of concentration. Also, a high percentage (approximately 40–50%) of the optic nerve may be damaged before a significant perceptual change can be detected on the visual field test, making perimetry relatively insensitive for detecting early damage when intervention may still save vision. Further, the visual field test is highly variable in areas of defects where damage has occurred, making it difficult to monitor changes.

Direct measurement of neuronal activity avoids the subjective nature of perimetry techniques, which require interactive perception reports from the patient. Traditionally, neuronal activity in the central nervous system including the retina has been recorded electrically. Recently however, noninvasive optical recording of neuronal signals from the brain has become possible. Intrinsic changes in the optical properties of active brain tissue (referred to as "intrinsic signals") permit visualization of neuronal activity when the surface of brain tissue is directly imaged using sensitive CCD cameras. Intrinsic signals refer to the fluctuations in the reflectance properties of tissue illuminated (or interrogated) by light. Such fluctuations result from changes in the absorption coefficient of the interrogated tissue due to the conversion of oxyhemoglobin to deoxyhemoglobin in response to the metabolic demands of active neurons. The interrogating light is band-restricted to wavelength(s) where the difference in absorption spectra between the oxyhemoglobin and deoxyhemoglobin molecule is the greatest, typically in the region of 580–700 nanometers (nm). Other sources of the intrinsic signals include changes in the microcirculation and light scattering, which are also dependent on neuronal activity.

The intrinsic signals from the brain are usually very small (0.1 to 1.0% of the overall reflected light intensity). However, when appropriately imaged, they can have high spatial resolution (50 microns) corresponding to the areas of active neuronal activity. The small intrinsic signals are isolated from noise using image subtraction or ratio techniques. By subtracting baseline (neuronally less active) images of the brain tissue from stimulated (neuronally active) images, (or taking the ratio of the images), small intrinsic functional signals can be isolated. With the use of optical techniques, it has been possible to record neuronal activities of the primate cortex in vivo. Perhaps the best example of optical recording of intrinsic signals in brain tissue has been the visualization of ocular dominance columns in the monkey primary visual cortex.

Visual cortical neurons that are driven preferentially by one eye are grouped into a strip of the cortex referred to as an ocular dominance column for the associated eye. Typically, an adjacent strip of cortical cells is driven preferentially by the other eye and forms an adjoining ocular dominance column. Strips of ocular dominance columns alternate between the right and left eye and form a prominent part of the functional architecture of the primate visual cortex. Ocular dominance columns were originally discovered through painstaking reconstruction of the locations and electrical responses of hundreds of individually recorded neurons. The optical recording of intrinsic signals has allowed the ocular dominance columns to be directly visualized across the cortex in vivo. This was achieved by imaging the cortex with interrogating light, while providing visual stimuli to one eye and then the other. Ocular dominance column images were then constructed by subtracting right eye-stimulated images from the left eye-stimulated images. Optical recording of the temporal lobe of human patients undergoing neurosurgery has also been reported.

New objective methods are needed to improve the sensitivity for detection of damage to the retina and optic nerve and change over time. Such methods would also provide more reliable determination of the status of the visual system. A number of new technologies have emerged in recent years in an attempt to fill this need and have included multifocal electroretinography (MERG) pattern electroretinography (PERG), visual evoked potential (VEP), multifocal visual evoked potentials (MVEP), and pupil perimetry.

A practical, highly sensitive and specific device for revealing retinal function is needed to aid in early detection of retinal and optic nerve diseases such as glaucoma and to monitor the progression of neuronal damage. This need is driven by the fact that standard glaucoma therapy of lowering intraocular pressure can reduce the rate of further optic disc damage. In addition, it would also be advantageous to be able to image the stimulus-associated activity of other layers of the retina, such as the deeper layers containing bipolar cells, photoreceptors and pigmented epithelium to assess the health of these layers in other diseases of the eye. It is these observations that have motivated the development a new functional imaging technique for the eye that would reveal activation of regions of the retina in response to visual stimuli.

SUMMARY OF THE INVENTION

An Optical Imaging Device of Retina Function (OID-RF) is disclosed. The device is constructed and arranged to record changes in reflected light from the ocular fundus caused by retinal activation in response to a visual stimulus. The resulting images reveal areas of the retina "activated" by visual stimulation. This device comprises a fundus camera designed to provide a patterned, moving visual stimulus to the subject in the green wavelength portion of the visual spectrum while simultaneously imaging the fundus in another, longer wavelength range. The change in reflected intensity from the retina due to the stimulus is calculated by comparison to the pre-stimulus state. A functional optical signal can be recorded from the human eye. The inventive device thus has the ability to directly measure the inner retinal function, rather than the outer retinal layer function.

In addition, the present invention can have a field of view of 45 degrees with 1000 pixels, or 0.5 degree-spatial resolution when a 12×12 pixel region is used for spatial averaging. This is an improvement over the spatial resolution of 1–2 degrees for the multifocal ERG. The system of the present invention can obtain functional signals rapidly (approximately 10 seconds for each iteration of stimulus response), so that there is ample opportunity to increase the signal-to-noise ratio (SNR) with multiple iterations, and thus increase the sensitivity of the instrument. Such a functional map of ganglion cell activity provides a means to detect a regional defect caused by glaucoma at an early stage, before visual perception or structural abnormalities become apparent.

BRIEF DESCRIPTION OF THE DRAWINGS

FIG. 8 depicts a table of correlation coefficients between Region 4, 5 (row 4, column 5) and other regions.

DETAILED DESCRIPTION OF THE INVENTION

Figure 1:
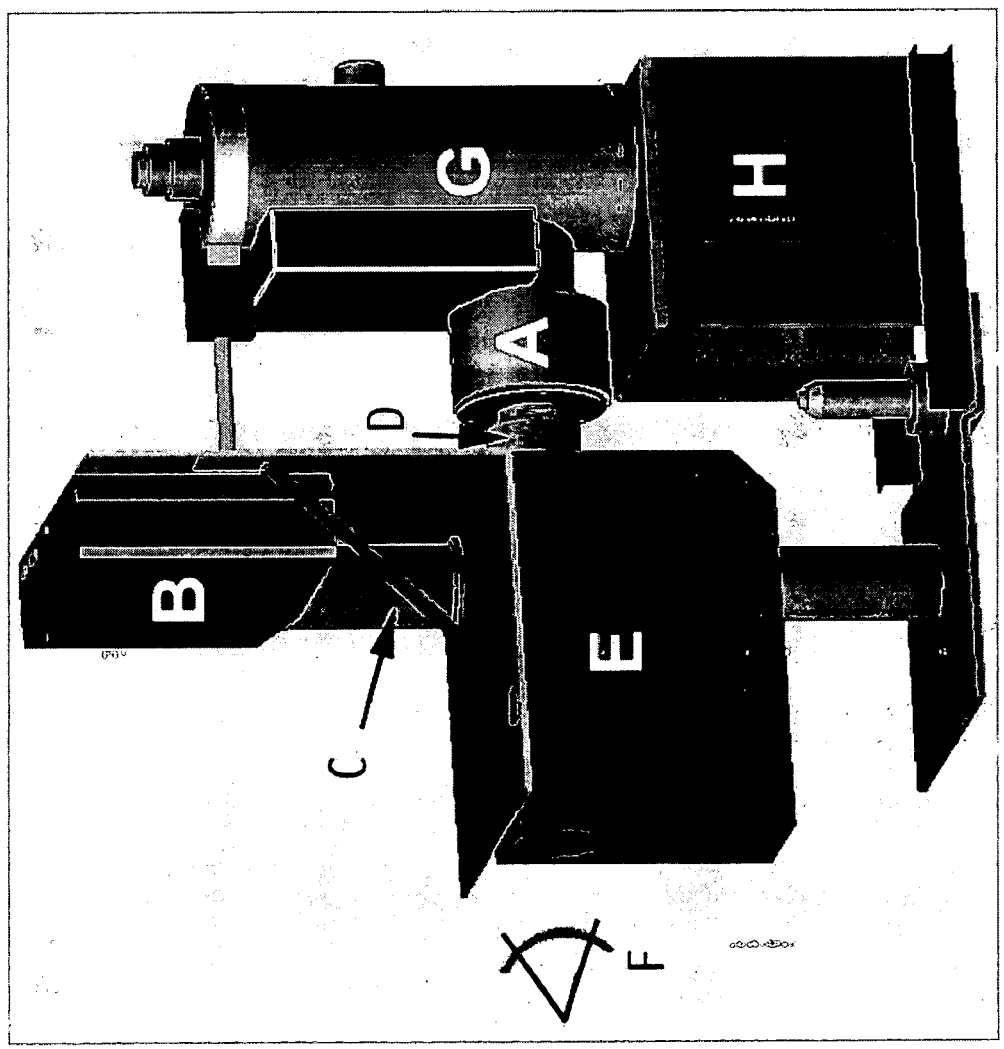
FIG. 1 is a schematic illustration of a preferred embodiment of an OID-RF device.
Figure 2:
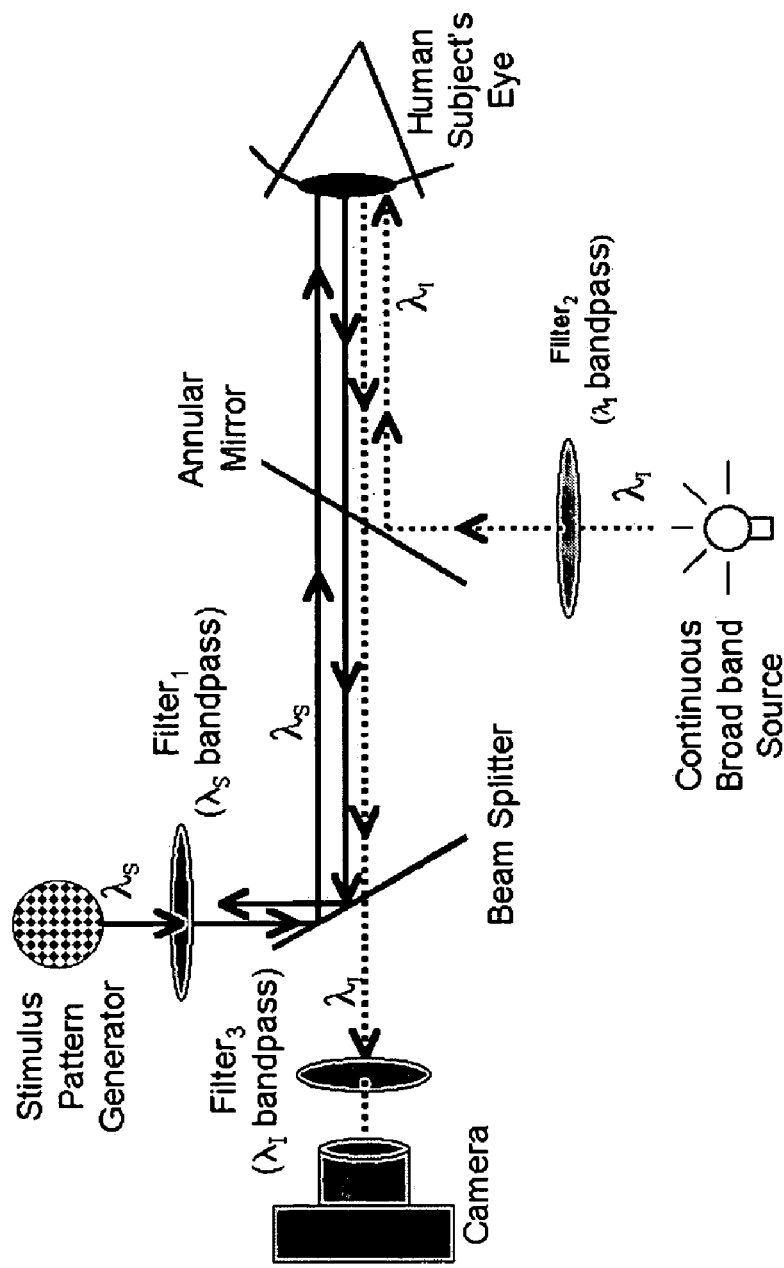
FIG. 2 depicts an optical layout of one embodiment of an OID-RF.

The optical recording of intrinsic neuronal signals is suited for objective assessment of retinal function. Like the cortex, neuronal signals from the retina can be recorded from a large area at once with high spatial resolution. Unlike cortex imaging, retinal imaging can be acquired directly through a dilated pupil or other area of the eye using an appropriate fundus imaging system. Optical recording of retinal function is noninvasive and ideal for clinical application.

Optical functional recording is possible in the retina because the retina is a direct extension of the brain and part of the central nervous system. Neuronal activity of the retina is fundamentally similar to that of the brain. Like the brain, appropriate metabolic changes (changes in hemoglobin oxygen saturation and state of tissue cytochrome for example) can be detected in the retina in response to changes in inspired oxygen levels.

The following steps are included in a preferred embodiment of an inventive method for the optical imaging of retinal function in the human eye:

1. local firing activity of retinal neurons in response to a light stimulus can be mapped across the two-dimensional plane of the retina by imaging the resulting changes in the reflected light in the spectral region of approximately 700 nm wavelength. In this spectral range, local changes in neuronal activity and oxygen may cause changes in the spectral reflection of light;
2. oxygen consumed by stimulated retinal cells causes a transient shift in the ratio of oxyhemoglobin to deoxyhemoglobin in the immediate microcirculatory region, which may include an initial depletion followed by a compensating increase, depending on how the light stimulus influences the metabolic demands of the tissue stimulated;
3. local changes in the oxyhemoglobin level can be imaged by detecting small changes in the absorption (and hence, reflection) in an active spectral band at baseline (pre-stimulus) and comparing this to the reflection during and after stimulus; and
4. retinal areas having reduced function can be identified as they show change in the spectral reflection of light at the same interrogation bands following a light stimulus as compared to surrounding areas of retina with normal function.

The optical measurements of local oxygen changes induced by neuronal activation are possible due to changes in oxyhemoglobin levels within blood vessels supplying the retina. A dense sheet of capillaries derived from the central retinal artery circulation provides the main source of oxygen to the inner retina, where the retinal ganglion cells and axons are located. It is these cells that produce electrical spiking activity or action potentials. A second circulation to the retina, derived from the choroidal circulation, supplies photoreceptors in the outer retina and part of the next layers of the retina. Unlike the inner retinal circulation, the choroidal circulation is a high-flow vascular bed with little change in oxyhemoglobin levels between the arterial and venous side under steady state conditions.

Figure 11:
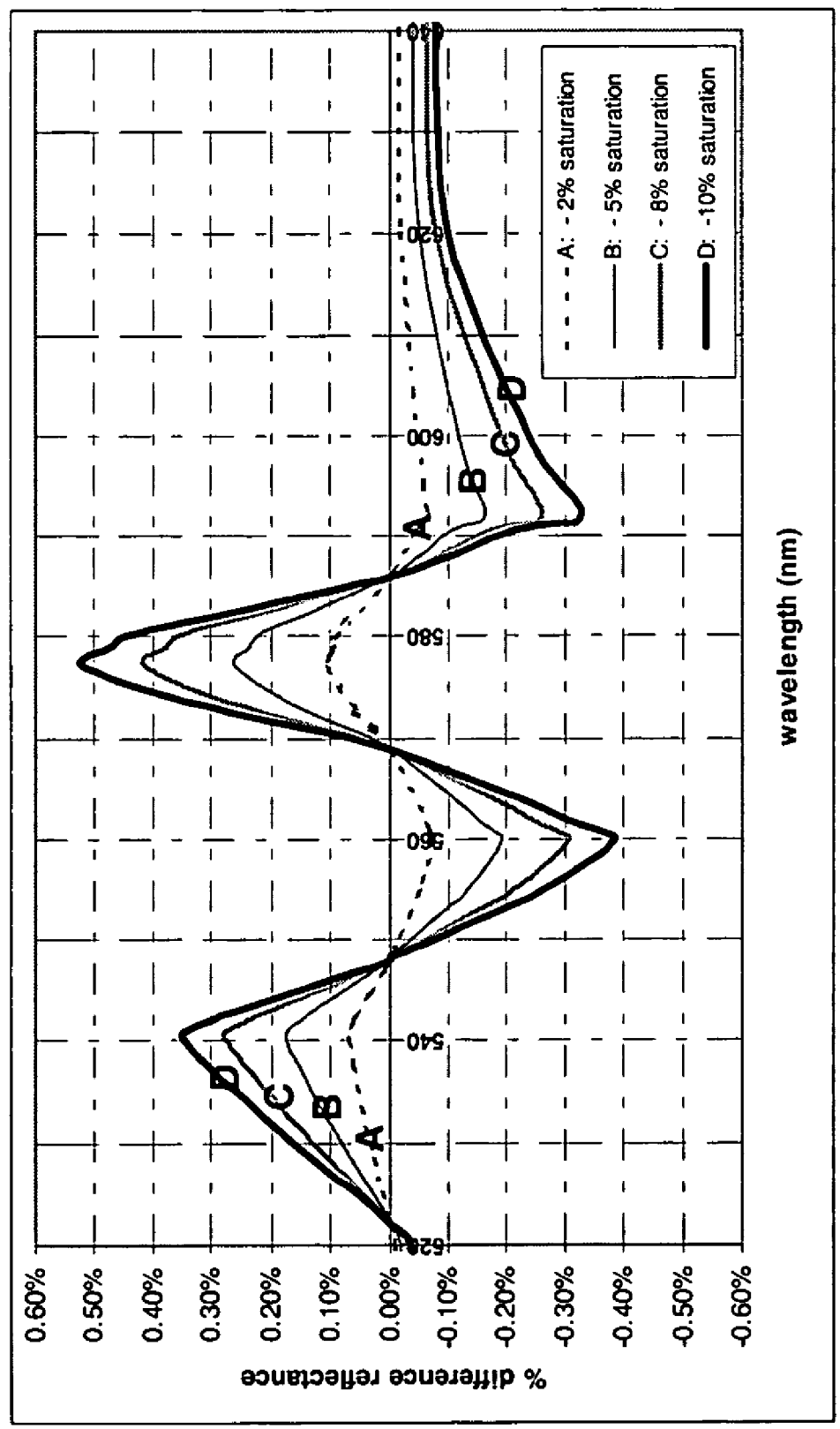
FIG. 11 depicts percent changes in reflected illumination.

The methodology for retinal functional imaging depends on the characteristic spectral properties of hemoglobin and its dependence on oxygen saturation. Spectral measurements of the ocular fundus and absorption spectra in FIG. 11 show the percent difference reflectance as a function of wavelength at various saturation levels of oxyhemoglobin. It is clear from FIG. 11 that a strategy can be devised to capture images at two or more wavelengths in order to measure changes in the oxyhemoglobin saturation for any retina regardless of its pigmentation or other biochemical and/or structural characteristics.

Equation (1) presents the analytical form of the radiation transfer. This equation, using absorption coefficients and typical optical densities, can estimate contributions of the oxyhemoglobin signal as measured by an OID-RF. The expected signal from a retinal arteriovenous difference for oxyhemoglobin would yield a measurable change in the reflectance spectra at 700 nm.

$$I_R = I_I 10^{-2\{\alpha_s D_s^R \mu^R + \alpha_u D_u^R (1-\mu^R) + \alpha_{RPE} D_{RPE} \alpha D_s^C \mu + \alpha_u D_u (1-\mu^C)\}}$$ (1)

where $I_R$ is the measured reflected light, $I_I$ is the incident light at the retina, $\alpha_i$ are the absorption coefficients, $D_j$ are the optical densities, and $\mu_k$ are the saturations. The S subscripts relate to the values at saturation and the U subscripts relate to the values for unsaturated hemoglobin. The R superscripts relate to the retinal layer and C to the choroidal layer.

Local changes in the reflectance of light in the spectral region indicative of the ratio of oxyhemoglobin to deoxyhemoglobin have been found to mirror local changes in neuronal function in brain preparations. The inventive approach is applied to the human retina. The time constant of small changes in reflected light is relatively long (on the order of 2–5 seconds following a visible light stimulus), which provides sufficient time to collect stimulus-evoked spectral intensity changes. Other faster changing signals may also be present and may also be a source of signal that could be monitored with faster collection rates.

Methodology and Instrumentation

In a preferred embodiment, an inventive method for optical mapping of retinal function comprises three steps:
1. stimulation of the retina in a selected spectral band (550 nm±12 nm) centered on the green cone maximum sensitivity;
2. measurement of the reflected intensity from the retina at interrogating spectral bands that reflect the state of hemoglobin saturation before and after stimulation. To maximize the signal to noise ratio (SNR), an interrogation wavelength centered on one of the bands of greatest difference, e.g. as 577 nm, 610 nm or 700 nm, is used; and
3. mapping of optical changes that result from retinal neuronal activity by registration of recorded video frames with subsequent subtraction of post-stimulation images from pre-stimulation images.

The approach employed by one preferred embodiment of the Optical Imaging Device of Retinal Function (OID-RF) is to selectively filter the continuous light source in a fundus camera to achieve an interrogation wave band. A stimulus pattern can be presented at one wavelength, for example 530 nm, and the oxy-hemoglobin change can be interrogated at a different wavelength, for example 700 nm, using the same optical path. The OID-RF device can be built using a Canon Fundus Photo Perimeter CPP-1. FIG. 1 shows the mechanical drawing of the OID-RF device.

Device Apparatus

A preferred embodiment of the inventive OID-RF device may include some or all of the following: 1) an optical stimulation of the retinal neurons, 2) an interrogating fundus illumination source to measure the reflectance changes associated with the decrease in oxyhemoglobin saturation, and 3) image collection by a camera.

Figure 12:
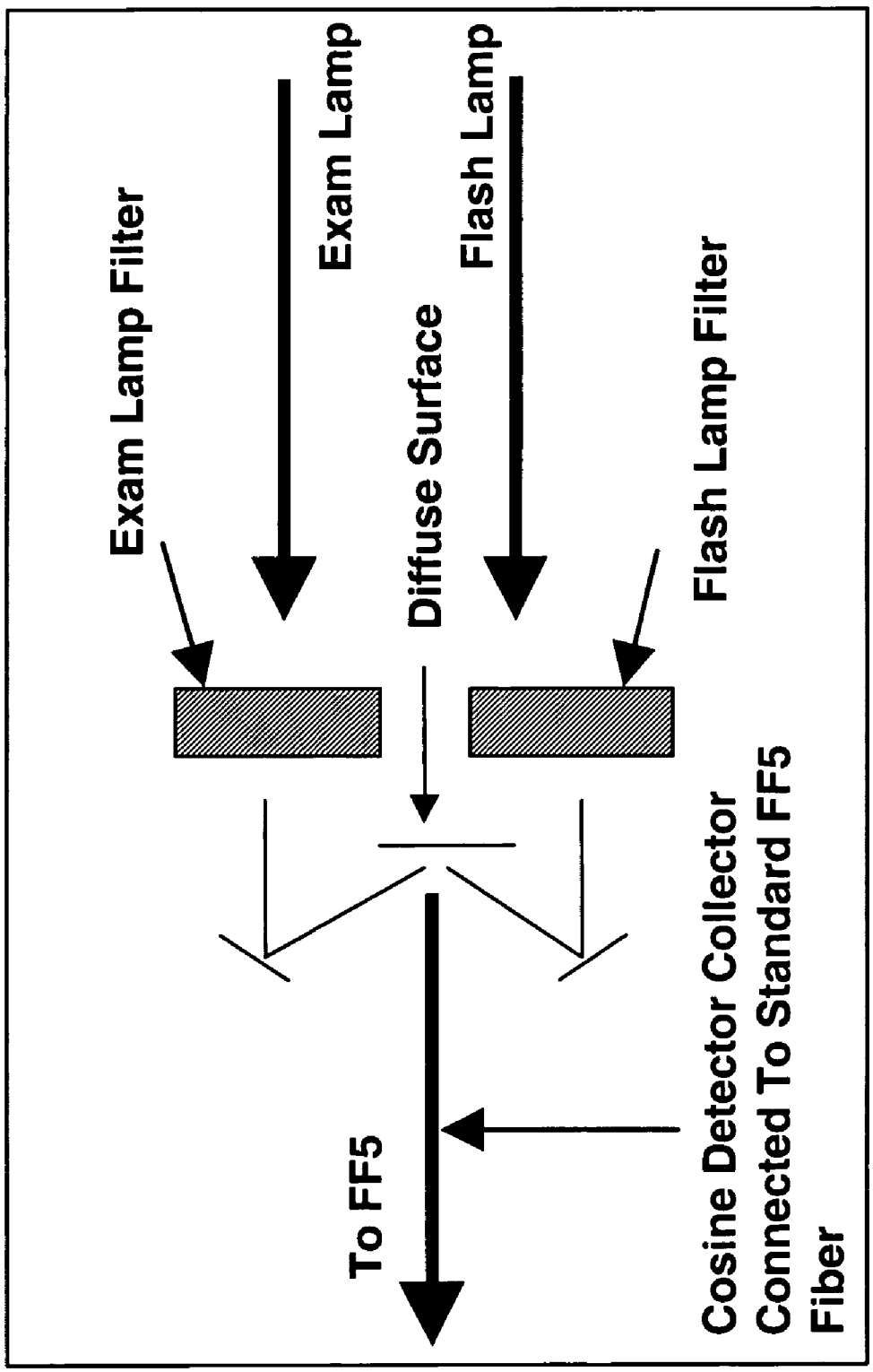
FIG. 12 is a schematic illustration of one embodiment of the device for filtering of illumination sources.

To make measurements, a standard Zeiss FF5 Fundus imager can be modified. The FF5 is particularly well suited for the proposed changes because it uses a fiber optic feed to bring in the flash and interrogation light used to illuminate the fundus. To provide the separate illumination sources, the power supply that contains the light sources can be modified to accept two fiber bundles, one set to collect the interrogating light, the other to collect the xenon flash stimulus. These bundles can then be brought to an intermediate optics processing enclosure, where the two sources can be individually filtered, and then combined into the standard fiber optics feed used in the FF5 (FIG. 12). This approach also permits the introduction of multiple filters in the interrogating illumination by making the filter holder rotate in synchronization with the camera framing rate. Alternating narrow band images can then be collected to permit observation of both the oxyhemoglobin signatures at 100 ms intervals.

The OID-RF may thus be constructed by taking an existing fundus camera and modifying the optical path by selectively filtering the continuous light source in the fundus camera to achieve an interrogation wave band. The system can use a stimulus pattern presented at one wavelength (550 nm), while interrogating the oxy-hemoglobin change at a different wavelength (580 nm, 610 nm, 700 nm, etc.), using the same optical path. The OID-RF device could also be built by modifying a Canon Fundus Photo Perimeter CPP-1. FIG. 1 schematically illustrates that OID-RF device. A structural framework can be used to couple two major components, the Charge Coupled Device (CCD) digital camera (marked A) and Liquid Crystal Display (LCD) stimulus (marked B) to the Canon camera. A narrow bandpass filter can be placed at C to direct only the stimulus wavelength to the subject's eye. Other filters to prevent the stimulus wavelength from reaching the sensor can be placed at D. Similarly, a longer wavelength notch filter can be placed at E to eliminate all but the desired interrogation wavelength from the broad-band tungsten source (marked E) in the Canon camera. A human subject's eye can be located at position F. G may comprise the liquid nitrogen dewar used for cooling the CCD sensor, and H may be a supporting structure.

In one embodiment, the digital camera may comprise a Roper scientific, back-illuminated CCD camera that has a format of 1340 pixels by 1300 pixels with 16-bit pixel depth. Thus, 65,536 levels of gray detection would be possible. This camera was selected because of the requirements for high sensitivity and resolution of very small changes in light.

A digital camera with the greatest sensitivity is of paramount importance. The Roper camera's flexibility was also a factor. To improve the sensitivity, multiple pixel binning (combining pixels before the read-out) of the camera signal was used. Tests have shown that a 8×8 binning with frame rates of 4 frames per second was optimal for our application. The result was a data set for each experiment with 52 frames, each containing 167×162 pixels.

The effect of changes in oxyhemoglobin saturation on measured reflected light can be estimated from Assendelft's extinction coefficients for saturated and unsaturated hemoglobin. The change in reflected intensity ranges from 1% for a 2% change in oxyhemoglobin saturation to 5.0% for a 10% change in saturation. To detect changes in reflected intensity in the order of 1.0% required that the OID-RF instrument have sufficient sensitivity to represent small grey-scale differences. These represented conservative estimates for changes in oxyhemoglobin that have been reported as high as 20%. Since digital camera with 8-, 12-, or 16-bit representation capacity will have increasing ability to discriminate the small changes that are expected, one preferred embodiment includes a 16-bit camera.

For the sensitivity assessment, the manufacturer's performance characteristics of the Princeton Instruments LN/CCD-1300 EB can be used. This sensor is a 1340 by 1300, back illuminated CCD with a electron read noise of 2 electrons, up to 750,000 electrons well capacity, less than 1 electron/pixel-hour dark current and 16 bits of dynamic range. The CCD detector has 20 micrometer pixels with close to 100% fill factor and is $LN_2$ cooled. Quantum efficiency has been measured at between 92% to 80%. Analysis of the radiometrics indicates that, within the limits of the data used in the assessment, there is a high probability of being able to observe as little as 0.1% change in oxyhemoglobin saturation changes.

Stimulus

Yet another preferred embodiment of the invention comprises an LCD projector (marked B on FIG. 1) coupled to a computer that produces the stimulus pattern. This allows one to quickly change the pattern design and presentation frequency. In a preferred embodiment, a high luminance LCD projector coupled to a computer can be used to provide the visual stimulus pattern to the retina at a spectral band centered on 530 nm.

In one preferred embodiment, the implementation of the visual stimulus can be via a standard PC-type computer driving a VGA video card with programming in a custom interactive language based on C. The stimulus computer communicated with the system controller computer via a RS-232 serial port. The VGA video card drove a LCD-type video projector that had been mounted on the Canon fundus camera, with relay optics that delivered the stimulus projected onto the subject's retina.

To provide the flexibility of different patterned and forms of stimuli, a liquid crystalline display (LCD) panel that is back-illuminated with a luminance source can be used. This can allow individual control of the spectral distribution and energy delivered to each of at least 300,000 distinct sites across 30–60 degrees of the retina. This is a significant advance over the art which discloses a crude hi-intensity flash/spot of light. Another preferred embodiment can use the LCD panel to deliver physiologically natural 20 candela/$meter^2$ of retinal activation with carefully controlled background levels designed to maintain the retina at a normal photopic (light adapted) or scotopic (dark adapted) operating state. In one embodiment, an LCD unit can be made similar to that found in "TV eyeglasses" that are typically sold to be able to view video and TV signals from a small LCD screen mounted in the frame of the glasses and imaged to each eye with a mirror. This LCD panel can be mounted in the optical path of a fundus camera to be able to provide a visual stimulus filtered in the green wavelength band of 540 nm+/−40 nm that falls on the desired field of view of the retina. A computer-controlled stimulus signal can be sent to the LCD panel to define the stimulus intensity, spatial frequency, stimulation frequency and synchronization with image collection by the CCD sensor. In another modification, an LCD panel taken from an LCD projector, which has a higher level of illumination possible, can be used.

The retina can be exposed to one spectral illumination level and source for the purposes of stimulation and another illumination level and source for the interrogation. Stimulation of the retina can be accomplished by presenting a stimulus in a specific, filtered narrow band (centered around 550 nm, near the peak of retinal sensitivity) that would cause normal areas of retinal neurons to fire, consume oxygen, and change the local microenvironment of oxygenated hemoglobin. In one embodiment, the retina can be stimulated and measured for 5 second intervals after a pre-stimulus baseline of 3 seconds is recorded. The stimulus period can be followed by an additional 5 seconds of recording. Involuntary eye blinks can be excluded in the averaging of frames following each stimulus. There can be no direct interference from the stimulation source (550 nm) on the interrogation (610 and 700 nm) wavelengths if the two bands are spectral separate from the stimulus band.

In another embodiment, the stimulus can be based on a moving concentric circular grating pattern, with a fixation point in the center. The grating can be rectangular in profile with a fundamental spatial frequency scaled with eccentricity, from 10 cpd in the parafovea to 0.2 cpd in the periphery (15–20 degrees out). The grating can move with an average temporal frequency of 2 Hz and can be near 100% in contrast. The intensity of the stimulus can be 100 cd/$m^2$. The stimulus spatial and temporal frequencies and intensities used are known to yield strong photopic stimulation of retinal ganglion cells and yet be completely within the safety limits of light exposure to the eye. The retinal illumination that used for both the stimulation and the interrogation can be well below that employed during standard fundus examination and photography.

A fixation target (small "+") can be placed in the field-of-view of the eye being examined. The fixation target serves to keep the subject's eye in a nearly constant position with respect to the stimulus pattern. The imaging cycle can be triggered from an external computer which interfaces with the LCD stimulus presentation and the CCD camera image collection. The spatial frequency, temporal frequency and intensity of the stimulus used, along with the stimulus wavelength, can be chosen to provide maximum stimulation of retinal ganglion cells while being completely within the safety limits of light exposure to the eye. The retinal illumination used for both the stimulation and the interrogation is well below that employed during standard fundus examination and photography.

The basic concentric grating stimulus can be programmed to move in a radial direction and can stimulate the entire retina or a given sector of it. In one embodiment, one of the two hemifields (e.g., superior and inferior hemiretina) in a given stimulus run can be selected. The hemifield retinal stimulation permits the provision of internal controls to ensure that the differential reflectance measurements correspond to the stimulated areas of the retina and that the simultaneously recorded non-stimulated retinal areas do not show the same change in optical signal. Other types of visual stimulus can also be used which may differ in color, timing, spatial structure, and brightness so that the stimulus may be tuned to preferentially weight the activation toward different layers of the retina.

Figure 16:
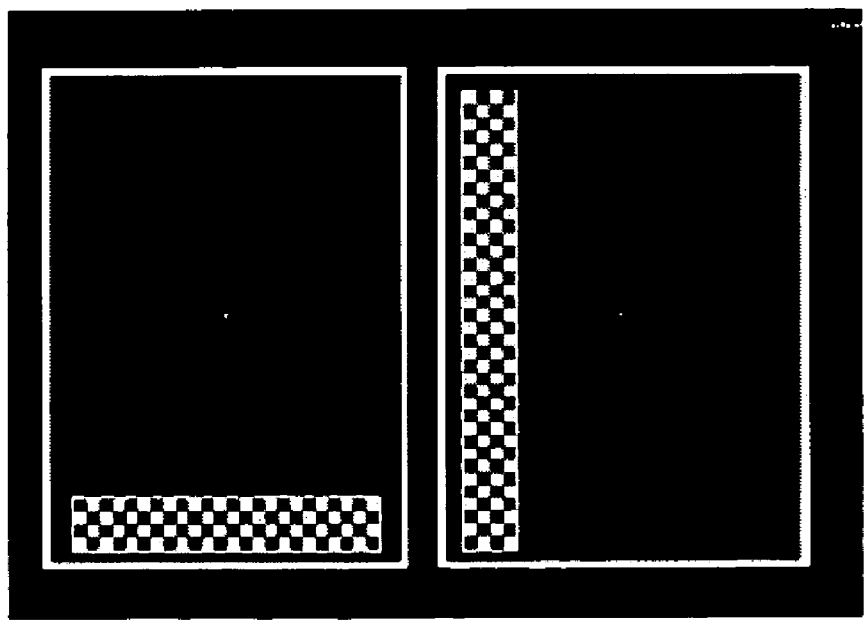
FIG. 16 depicts an example of a vertically oriented and horizontally oriented bar with checkerboard pattern used for a visual stimulation of a cat's retina.
Figure 21A:
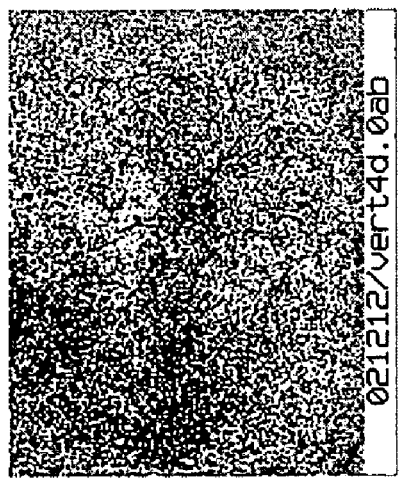
FIG. 21a depicts decreased spatial frequency of a checkerboard pattern on a bar.
Figure 21B:
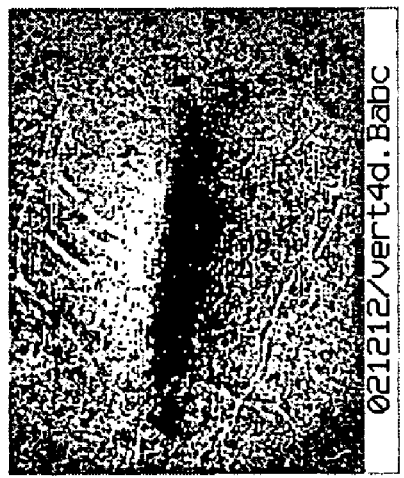
FIG. 21b depicts increased spatial frequency of a checkerboard pattern on a bar.

FIG. 16 depicts an example of a vertically oriented and horizontally oriented bar with checkerboard pattern used for a visual stimulation on a cat's retina. The stimulus in this case was left on for 5 seconds and compared to a baseline state of no stimulation. For separate experiments the bar was moved to a different location on the retina. Results are presented in FIG. 19. In other experiments, the spatial frequency of the checkerboard pattern on the bar was changed to be either coarser or finer (see FIGS. 21a and 21b.) FIGS. 21a and 21b depict an example of how changing the spatial frequency of the pattern of the stimulation bar affects the functional signal. In FIG. 21a, the spatial frequency was decreased (the checkerboard pattern was made larger and coarser), and this caused a less distinct area of functional activation. In FIG. 21b, the spatial frequency was increased (checkerboard pattern was made smaller and finer), and this caused a much more discrete area of functional activation with sharper edges.

Effect of Stimulus Characteristics on Functional Signal and Retinal Layer being Measured.

One skilled in the art will recognize that a combination of a variety of moving, patterned visual stimuli that select responses from the outer and inner retina (photoreceptors/ pigment epithelium vs. ganglion cells) can be used. This may be accomplished by stimulating one layer during the baseline period and during the stimulus period, add a stimulus attribute that enriches the metabolic activity of the retinal layer that is desired to be sampled. Thus, a combination of baseline stimulus compared to the stimulus during an activation period reveals the layer of the retina that was activated above the baseline stimulus. As a non-limiting example, the baseline lighting condition can be more of a diffuse, luminant stimulus that primarily causes activation of the photoreceptors and then an added stimulus during the activation period can have attributes (i.e. pattern, form, movement) that cause an added activation of the inner retina, containing the ganglion cells. This produces a functional signal that is from the inner retina and has the spatial distribution on the retina that is similar to the stimulus shape and location. Results of this are depicted in FIGS. 18, 19, 20, 21a, and 21b. Moreover, changing the spatial frequency of the pattern of the stimulus (how fine or coarse it is) can also affect the strength and sharpness of the borders of the functional signal, corresponding to the activation of the inner retina containing ganglion cells whose response is dependent on spatial frequency (FIGS. 21a and 21b).

Alternatively, giving a baseline pattern stimulation or no stimulation during baseline followed by a diffuse non-patterned stimulus during the stimulus phase may more selectively reveal function of the outer retina containing the photoreceptors. Because the outer layer of the retina consumes an increase in oxygen during darkness due to the energy requirements of restoring the cell membrane ionic potential by an ion pump, functional activation of the outer layer can also be observed using a dark period as the stimulus. Subtracting or taking a ratio of the baseline images compared to the activation images can yield any activation (and hence functional signal) that occurred in contrast to the baseline stimulation. This approach provides a new method of selective optical functional imaging of one layer of the retina over another by selecting a specific attribute of the stimulus during the baseline period and during the stimulation period.

In another embodiment, the selective activation of one layer of the retina compared to the other can be achieved by varying the stimulation frequency of the light (how fast the stimulus is changing contrast or luminance). For example, it has been found that electrical potentials evoked from the inner retina (mainly ganglion cells) using pattern electroretinography (PERG) gives a maximum electrical signal when a spatial pattern is alternated at 14 Hz. Therefore, the frequency of light can be used as another parameter that is intended to enrich the functional signal for different types of retinal cells in different layers that respond differently to the frequency of light.

In yet another embodiment, different wavelengths of the stimulus light can be used to activate different classes of photoreceptors and the retinal neurons that they subsequently activate. Therefore, the color of the stimulus light is another method that can be used to activate different classes of retinal cells.

Stimulation Light

A bright, 2–7 ms, computer-triggered stimulation can be obtained by narrow band filtering the output from a xenon flash lamp. The narrow band filter centered on 531 nm can be placed within a custom-built filtering module. A non-limiting example is depicted in FIG. 12. In one embodiment, a corresponding method using such a stimulus may include the following steps:

1. increase in the number of stimulus flashes to 10 or 15 flashes in a row per cycle
2. increase the stimulation frequency by configuring a strobe light coupled to the fiberoptic so those stimuli can be given at a faster rate than one per second It is possible that the retinal ganglion cells can be more optimally stimulated using a patterned stimulus rather than a uniform stimulus. A skilled practitioner will recognize other means of stimulating the retina. For example, one embodiment can include alternating bar or checkerboard patterns into the optical path of the fundus camera in a series of stimulus-interrogation cycles like those described in the methods above. This can be accomplished by replacing the incoherent fiber optics of the Zeiss FF-5 fundus camera with coherent fibers capable of transmitting an image. A focus is then created in the filtering module where a spatial element is introduced. The diffuser in the module can be replaced with an optical surface and the interrogating and flash illumination is recombined and sent to the FF5 with the flash now being spatially distributed.

In another embodiment, the retina can be stimulated by short, relatively bright xenon flashes in a specific, filtered narrow band (centered around 531 nm) that will cause normal areas of retinal neurons to fire, consume oxygen, and change the local microenvironment of oxygenated hemoglobin. The retina can be stimulated at 1 second intervals by the xenon flash in the fundus camera.

A bandpass filter centered at 531 nm placed in front of the xenon flash can selectively stimulate the retina by presenting a wavelength at the peak of the retina's spectral sensitivity. A fixation target viewed by the unstimulated eye can allow the subject to maintain eye position during the stimulus and collection period. Involuntary eye blinks can be anticipated to occur with a latency of 100 ms after a bright flash and will therefore, not interfere with the amount of light reaching the retina. Fundus images obtained during an eye blink will be discarded and not included in the averaging of frames following each stimulus.

In one embodiment, each stimulus cycle may comprise 5 flashes followed by 5 seconds of recovery period. The cycle can be repeated 10 times to allow for signal averaging. It is expected that the optical response of the retina to the stimuli will increase from baseline over the ensuing 2–5 seconds. The flashes of light can be triggered from an external computer, which interfaces with the power supply of a Zeiss FF-5 retinal fundus camera. This Zeiss FF5 fundus camera's light source for stimulation and observation are external and uses a fiberoptic connection between the power supply/light source and the fundus camera to illuminate the subject's retina. This arrangement allows for flexibility in modifications of the light source, as necessary.

In another embodiment, a dichroic beam splitter can be used to optimize transmission of stimulus and interrogation light. A specially coated dichroic beam splitter can be designed to allow a selected part of the spectrum (shorter stimulus wavelengths) to be reflected and the remainder of the spectrum to be transmitted (longer interrogation wavelengths). This dichroic beam splitter will allow nearly 100% of the stimulation light to be directed to the eye, as opposed to the 15–20% that is otherwise transmitted as stimulus. Similarly, the reflected interrogation light can pass through the beam splitter without significant loss of intensity.

The improved optics are used to simultaneously increase the effectiveness of the stimulus delivered to the subject eye and allow more of the reflected interrogation light to reach the detector. The increased stimulus intensity gives more flexibility in stimulus experiments, while the improved throughput of the interrogation light to the detector allows for shorter integration times and higher frame rates, less interrogation light incident on the subject eye, and less stringent requirements for camera cooling and sensitivity. A custom dichroic splitter can significantly increase the effectiveness of the stimulus reaching the subject's eye. The optical delivery path for the stimulus can be optimized through the use of custom optics and improvements in projector stability and adjustment capabilities.

Method and Device for Interrogation of the Retina

In one embodiment, the interrogation light can be from a low intensity ($10^{-4}$ watts/nm) examination lamp from the fundus camera. The retina can be continuously illuminated with the interrogation light throughout the cycle.

In another embodiment, the interrogation light source can be from a tungsten examination lamp from the fundus camera. The retina can be continuously illuminated with the interrogation light throughout the cycle. During the periods before (baseline) and after the stimulus (the recovery period), images of the entire 45 deg field of view can be captured.

In yet another embodiment, the interrogating light for the fundus can be provided by the external tungsten lamp of the Zeiss FF-5 with a constant level light source. A rotating filter wheel, as describe above, can be placed within the filtering module to allow the retina to be interrogated at two alternating wavelengths.

Figure 13:
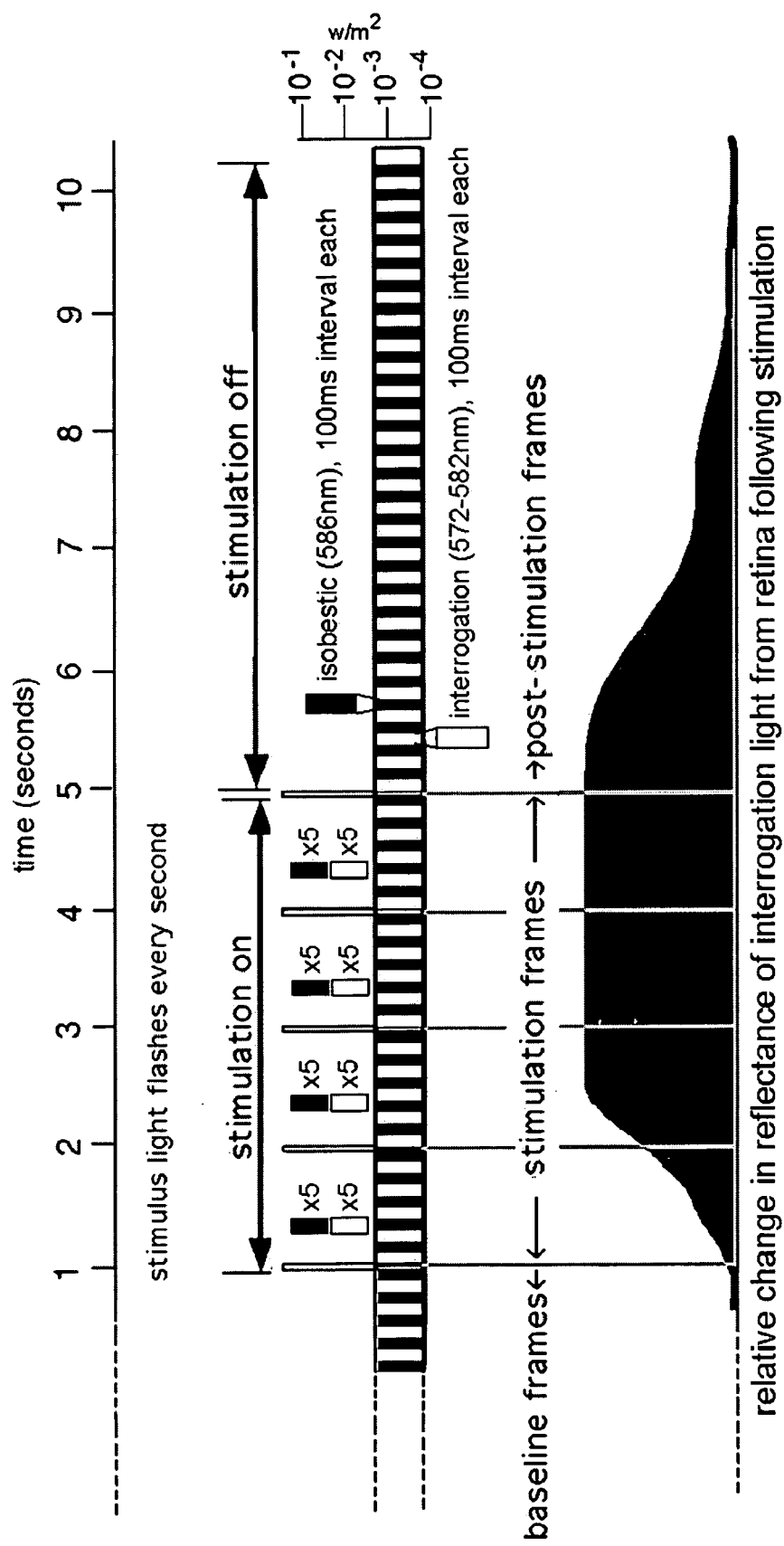
FIG. 13 depicts an exemplary interrogation and a stimulus profile.

Initially, the interrogation light can cause some stimulation of the retina, prior to time=1 in FIG. 13. Within a short period, the retina will become adapted to the interrogation light. During the period between flashes as well as after flashes (during the recovery period), spectral interrogation images of the entire 30 deg. field of view can be captured by the 16-bit, low-noise CCD camera (as described above).

These interrogation images can consist of two rapidly alternating spectral regions; an isobestic wavelength (unaffected by changes in oxyhemoglobin saturation) and "active" spectral bands, (where the absorption is affected by changes in oxyhemoglobin). This can be achieved using a rotating filter wheel placed in front of the interrogation light and synchronized by an external computer. Each image can be collected for 100 ms duration (10 Hz) to minimize image blur due to small involuntary eye movements. Thus, each 1 second interrogation period can contain a total of 10 image frames (5 frames at an isobestic wavelength and 5 at the active wavelength).

To decrease the interfering effect of the choroidal circulation, which lies under the pigmented epithelial layer of the retina, one of the shorter interrogating wavelength bands (for example 555–565 nm or 572–582 nm range instead of the longer 590–610 nm band) can be used. At the shorter wavelengths, the pigmented epithelium blocks most of the light from reaching the choriocapillaris, but this range is still in the spectral region that changes with oxyhemoglobin saturation.

Figure 14:
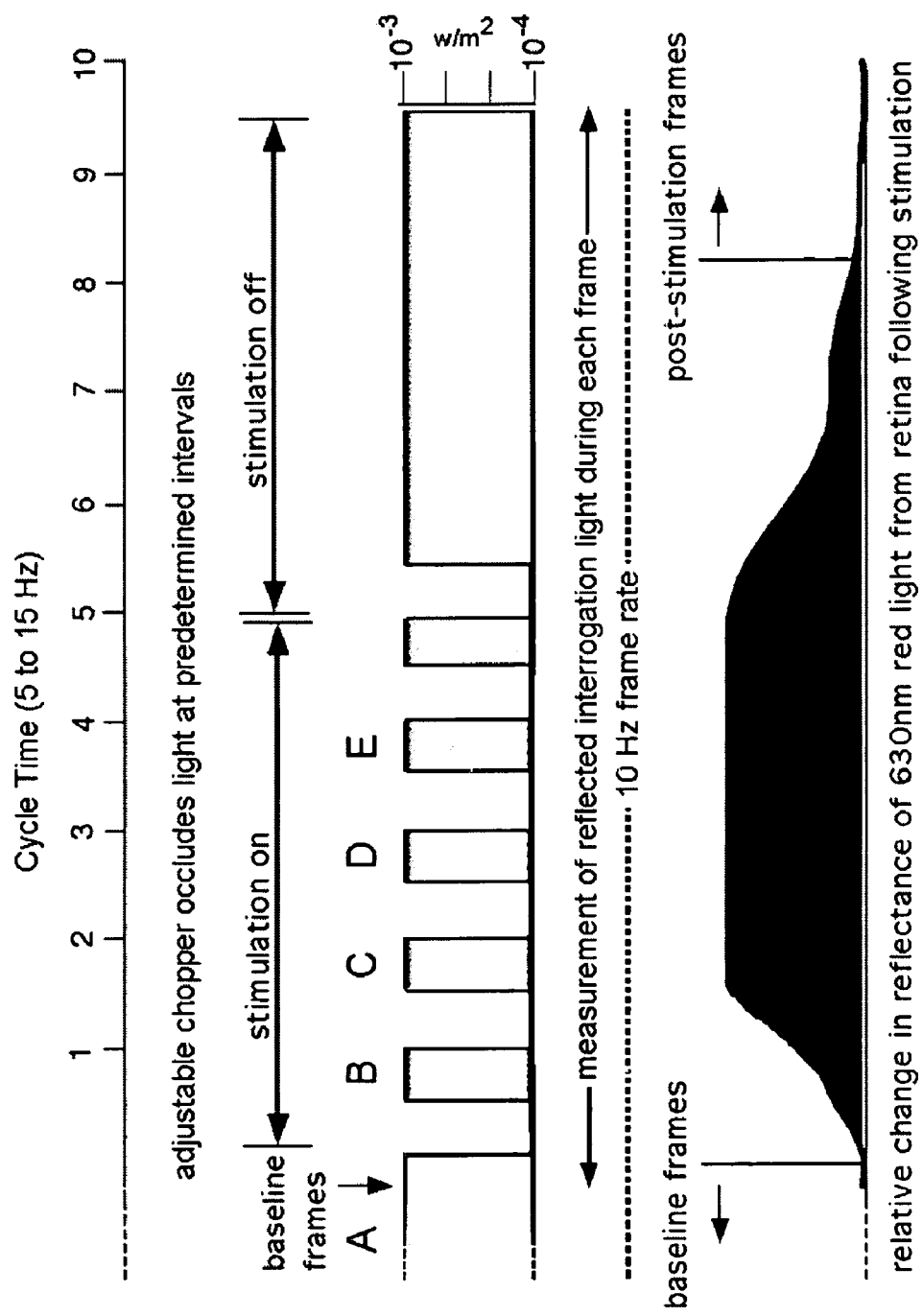
FIG. 14 depicts an exemplary interrogation and a stimulus profile.

In another embodiment, If the interrogating light is not bright enough to fill the majority of the 16-bit pixel wells in the CCD camera, the intensity of this light can be increased and used as the stimulus light at the same time. In this embodiment, the bright light would be "chopped" using the rotating shutter wheel at a fast speed so that the retina will see an "on" and "off" stimulus, which provides better stimulation than a continuous light (FIG. 14). This wheel will allow both selectable chop frequency and illumination duration and can be controlled through a computer interface to the overall camera controller and data manager.

In one embodiment, the optical path marked—follows the principal ray of the interrogation light (G). The interrogation light can be injected into the optical path so that the subject's retina is illuminated by a longer wavelength, independent of the stimulus wavelength. As described above, the percent of the interrogation light reflected from the retina changed depending on the hemoglobin oxygen saturation. The reflected light can be directed back to the beam splitter (B), where approximately 85% can be passed to filter (D) and then to the CCD camera. The 700 nm (40 nm bandpass) filter in front of the CCD camera can be configured to allow only the reflected intensity from the interrogation light. In this manner, the OID-RF's optics and filtering permit the stimulation of the retina with a pattern at one wavelength and interrogate the reflected intensity at another wavelength.

One skilled in the art will realize that certain modifications could be made. One embodiment can integrate regulated power supply for interrogation light. The present invention can make use of a highly stable regulated power supply for the interrogation light. This type of power supply is necessary to ensure that the illumination is constant and that observed variations are not due to changes in incident light. One embodiment can employ a 12-Volt regulated power supply to allow for greater illumination range. In order to improve system compactness, this new regulated power supply can be integrated into the base of the Canon in the space formally occupied by the original unregulated power supply.

Method of Delivery of Retinal Illumination for Interrogation with Near Infrared Light In one embodiment, the retinal interrogation light can be accomplished by employing a transcleral and/or transdermal illumination of infrared and/or near infrared light source to interrogate the functional signals from the retina. The infrared light (700–900 nm range) can be transmitted through the skin of the lower eyelid and inferior orbital area next to the orbital bone using a single or cluster of infrared emitting diodes applied perpendicular to the skin.

Alternatively, the light can be aimed through the sclera a short distance away or directly applied to the sclera via a contact lens using infrared light emitting diodes. This method is not an obvious alternative to illumination through the cornea and pupil. Experimental results used 700 nm light that was shined through the cornea and pupil and show that a large source of noise (reflectance fluctuations from the retina) can be caused by small eye movements, made involuntarily by the patient during the collection period. Changes in the corneal tear film from evaporation of tears can also affect the reflectance on the retina. Illuminating the retina through the sclera and not through the cornea can reduce this coupling noise of the incident light compared to the reflected light from the retina.

Method for Retinal Interrogation using Plural Wavelengths

One embodiment can use broad band retinal interrogation light in the near infrared wavelength range which is seen as a dull red background and that is barely visible (780 nm band+/−40 nm). At this wavelength region, the near infrared light passes through all layers of the retina, including the deepest layer, the pigmented epithelial layer. Other interrogating bands at shorter wavelengths that do not penetrate the pigment epithelial layer as well can also be used, and hence are not influenced as much by the underlying circulation (and hemoglobin) of the choroid. Therefore, one embodiment utilizes different interrogation wavelength bands to allow probing functional signals from different layers (and vascular beds) of the retina due to the differing absorption properties of the retinal layers.

Specifically, the retinal pigment epithelium, which contains melanin, reflects shorter wavelengths but allows longer wavelengths to be transmitted to the next deeper layer, the choroid, which contains the vascular layer of the outer retina. For example, the inner retina (ganglion cells and axons, amacrine cells, and the bipolar cells) is primarily supplied by a superficial inner capillary layer derived from the central retinal artery, whereas the outer retina is supplied by the choroid, derived from the posterior ciliary arteries. Therefore, the influence of these two vascular layers on the functional signal are preferentially interrogated depending on the penetration of the interrogating light, which is influenced by its wavelength.

In another embodiment, a longer wavelength of interrogation light that is further from the visible spectrum can be used to improve the functional signal by providing less interference with the visible spectrum range that is used during the stimulation phase of functional imaging. This is because near infrared wavelengths that are still well within the light spectrum that is visible to the eye (perceived as red) will still act as a stimulus and may reduce the component of the signal due to further stimulus activation on top of that stimulus (during the stimulation phase of testing). Use of broader bands of interrogation light on one side of the infrared isobestic point for oxyhemoglobin/deoxyhemoglobin spectral changes will also help to collect more reflected light to the sensor.

Preliminary data obtained from the cat and monkey retina indicates a very reproducible functional signal using and interrogating wavelength band of 780 nm+/−40 nm. Therefore, the wavelength spectrum of the near infrared and infrared interrogating light can be used to greatly influence the functional signal. In one embodiment, a wide (+/−40 nm) band-width can be used to provide more energy of light falling upon the sensor of the camera, making small changes due to functional activation more easily detected above a background of noise. This method, therefore, includes optimizing the functional signal from a given layer of the retina by choosing a specific wavelength and band-width for interrogation.

In another embodiment, the illumination of the retina with the interrogation light has been sits on the edge of visibility and yet avoids the 810 nm hemoglobin isobestic point where the oxymetry and blood volume signals would cross and begin to interfere. The band of 780+/−40 nm allows high light delivery, no patient discomfort (it is barely visible) and reasonable quantum efficient for CCD cameras, in addition to reasonable intrinsic signal amplitude. In yet another embodiment, wavelengths in the "far red" (near infrared) that are visible but appear as dim red are used and 1) can serve as a steady luminance background to place the retina in a stable metabolic state, at photopic adaptation levels 2) do not interfere with retinal activation utilizing visible stimulation at shorter wavelengths, 3) can be optimized for high light efficiency in our optics and camera and result in easily detectable intrinsic signals.

To effectively detect small changes in the amount of near infrared light reflected from the retina, a suitable amount of near infrared light must fill the wells of the CCD sensor. To accomplish this one embodiment includes a CCD camera that is both very sensitive to small changes in light and which contains deep wells (large capacity to collect a large amount of light) with adjustable frame-transfer exposure control.

Data Acquisition System

The acquisition system may include at least one Pentium-based computer. In one embodiment of the system, one using two computers, the first computer can operate under Microsoft Windows NT acting as system controller, and the second computer can run Microsoft DOS producing the video output for the stimulus pattern. A 16-bit liquid nitrogen cooled Roper Scientific data camera and its related interface can also be included in the acquisition system.

In some embodiments of the system, the system controller can orchestrate all data acquisition activities. This controller provides a graphical user interface (GUI) for setup and monitoring of the data acquisition process. Parameters such as the length of time for the initial, stimulus, and final periods, camera binning and integration (exposure), stimulus pattern settings, and ancillary data such as subject ID, eye imaged, and filters used can be entered.

In one embodiment, the information provided on period times and binning can be used to compute the number of required frames, and that value, along with the binning and exposure, is sent to the data camera controller. The selected binning values and integration time are used in conjunction with a lookup table to compute an approximate frame rate. The period information and corresponding frame rate are used by the system controller to determine at which frames the stimulus should be presented to the subject.

The system controller can monitor one or more contact closures. In a preferred embodiment, the system controller can monitor one via a footswitch, a trigger on a joystick, as well as a GUI button on screen, and commence data collection in response. The system controller issues a start command to the data camera, and from that point the data camera collects the specified number of frames. Frames are displayed on the system controller's monitor as they are acquired and can be re-displayed after collection if desired.

As data collection proceeds, the system controller can poll the camera for the current frame. When the appropriate frame is reached, the system controller can signal the stimulus computer via RS232 or another communication means to display the pattern. Upon reaching the end of the stimulus period, the system controller issues another command for the stimulus pattern to be discontinued.

Once all frames of the current epoch are captured, the camera can automatically save the data as a multi-frame image to a file with name as specified by the system controller. After data acquisition is complete, the system controller can produce a second file in ASCII format with name corresponding to that of the image file. This ASCII file can contains parameters used during the acquisition, including information on the stimulus pattern and orientation, camera temperature, actual measured time periods and frame rate, and ancillary data provided by the user.

Figure 4:
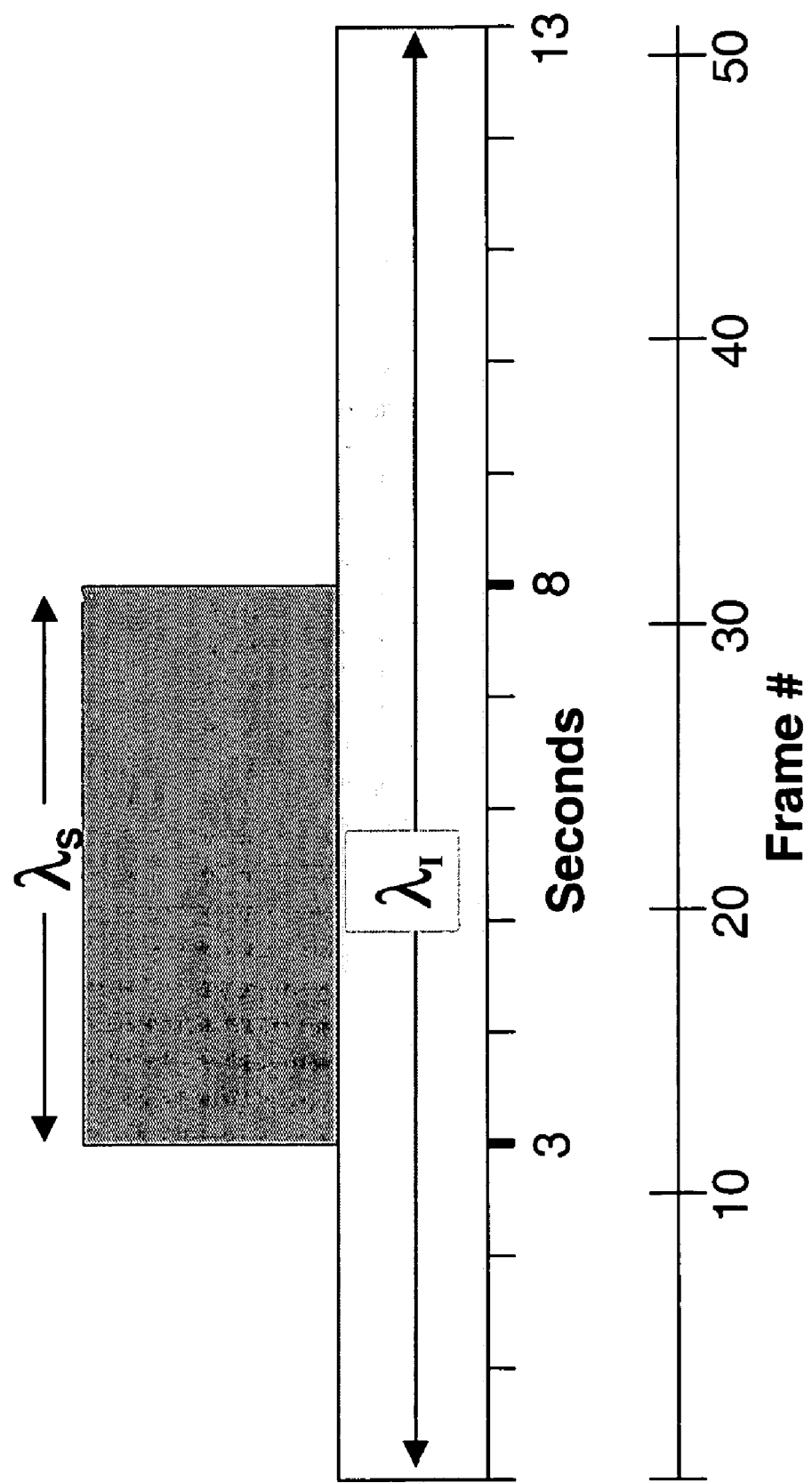
FIG. 4 depicts a typical data collection epoch.

According to a preferred embodiment of the invention, a data collection epoch is repeated an average of 10 times for each eye with rest periods between epochs. FIG. 4 depicts a 13 second epoch comprising a 3 second recording of pre-stimulus baseline, a 5 second stimulation and simultaneous measurement period, and a 5 second recovery period. Involuntary eye blinks are not included in the averaging of frames following each stimulus. There is no direct interference from the stimulation source (530 nm) or the interrogation (700 nm) wavelength since the two bands are separated using internal filters. If other wavelengths are used in visual stimulation and interrogation, appropriate blocking filters can be used to separate the two light paths.

To maximize the signal to noise ratio (SNR), an interrogation wavelength in one of the bands of greatest difference, such as 555–565 nm, 572–582 nm or 590–610 nm can be compared to an isobestic wavelength. Reflectance at isobestic wavelengths (zero crossings at 527, 569, and 586 nm in FIG. 11) is independent of changes in oxyhemoglobin saturation. The difference in reflectance at these two sets of wavelengths can be attributed to the changes in oxyhemoglobin saturation. Thus, the isobestic wavelength provides a reference from which to measure only the changes in oxyhemoglobin saturation. For example, changes in the amount of light impinging on the retina could change due to any instability in the light source or in eye position. By comparing the intensity at the isobestic point with the intensity at a wavelength that does reflect the oxyhemoglobin saturation, these random fluctuations can be eliminated, increasing the signal to noise ratio of optical signals.

Image Collection

Data can be collected every 100 ms by observing in-band the fundus reflections using a camera. In one embodiment, the camera can be a CCD camera. The use of a 1,000 by 1,000 pixel format camera can swap field of view for spatial resolution. When set to observe a full 30 deg field of view, the spatial resolution will be approximately 15 micrometers. Since the Pixel Vision camera is not a standard format CCD, a set of relay optics can be used to transfer the normal FF5 focal plane to the Pixel Vision detector. These optics can be housed with the camera and attached to the FF5 through its standard camera view port.

To make the measurements used in the proposed analysis, a standard Zeiss FF5 Fundus imager can be modified. The FF5 is particularly well suited for the proposed changes because it uses a fiber optics feed to bring in the exam and flash lamp used to illuminate the fundus. To provide the separate illumination sources, the power supply that contains the light sources can be modified to accept two fiber bundles, one set to collect the exam lamp light, the other the flash lamp light. These bundles are then brought to an intermediate optics processing enclosure, where the two sources are individually filtered, and then combined into the standard fiber optics feed used in the Zeiss FF5 (FIG. 12). This approach also allows the introduction of multiple filters in the exam lamp illumination by making the filter holder rotate in sync with the camera framing rate. Alternating narrow band images can then be collected to allow observation both the isobestic and interrogating wavebands at 100 ms intervals. To accommodate the second mode of operation, a chopper wheel can be placed immediately after the filter. This wheel can allow both selectable chop frequency and illumination duration and can be controlled through a computer interface to the overall camera controller and data manager.

In one embodiment, the camera can be controlled by a separate PC based computer interface that operates the FF5 illumination sources and the camera. The Pixel Vision camera produces 2 Mbytes of data per frame for a 20 Mbyte per second data rate at 10 frames per second. The image data can be sent directly to a local RAM over a dedicated high speed VSB bus. A single 512 Mbyte RAM card will allow storage of over 20 seconds worth of imaging. After collection the data will be transferred to a disk for archival and processing.

Calibration measurements show that the OID-RF system can be operated at less than 0.1% frame-to-frame variation in reflected light intensity measured from a stable source of reflected light. The CCD camera that performed the functional imaging and the LCD projector that was used for patterned stimuli can be integrated.

Method for Reducing Effect of High Reflectance of Optic Disc Portion of Retinal Image The optic nerve, which is within the fundus image, can cause a great deal of reflected 700–900 nm light that can reduce the quality of the image from the rest of the fundus (retina). One method known to those skilled in the art to compensate for this requires a reduction in the intensity of the interrogating near infrared light but reduces the signal to noise ratio of the functional images.

The present invention achieves reduction of the optic disc reflection by using an "Allen dot", which is a small obstruction that can be placed in part of the optical pathway to block the optic nerve head reflections. This approach of masking the highly reflective optic disc can allow increased illumination intensity to increase the signal to noise ratio of functional images, without running into the problem of confounding reflections from the optic nerve head.

CCD Imaging

The effects on measured reflected light due to changes in oxyhemoglobin saturation are shown in FIG. 11. That these reflected intensity changes range from 0.1% for a 2% change in oxyhemoglobin saturation to 0.5% for a 10% change in saturation. In one embodiment, the OID-RF instrument can have sufficient sensitivity to represent small gray-scale differences to detect changes in reflected intensity on the order of 0.1%. A digital camera with 8-, 12-, and 16-bit representation capacity will have varying ability to discriminate the small changes that are expected.

Additionally, the performance of the CCD camera itself is a factor. To determine the required sensitivity to measure these changes, the spectral radiance of the Tungsten exam lamp can be measured. For the sensitivity analysis the preferred characteristics of commercial cameras such as the Pixel Vision SV series, or Photometrics Series 300 can be used. These CCD cameras have a full well of 325,000 electrons (950,000 electrons serial registration full well), 16-bit digitization, 80% quantum efficiency over the band of interest, and less than 1 electron of dark current. These CCD cameras have about 4 electrons of read noise when cooling is augmented with a liquid nitrogen heat exchanger, and a 24 μm pixel. Higher performance can be obtained by using a custom camera such as those used in atmospheric compensation applications where the read noise is reduced to 2 electrons with less than 1 electron of dark current and the full well is increased to over 500,000 electrons.

If a 20 nm wide band around 600 nm is used for integration, the number of photons reflected back to a camera pixel from the fundus approximately $$N_{\Delta\lambda} = t5.034 \times 10^{15} \int_{600}^{620} R_\lambda n \Phi_\lambda d\lambda$$

where n is the index of refraction (about 1.3), dλ is the waveband (600 nm to 620 nm in this case), t is the exposure time, $R_{80}$ is the reflectance from the fundus, and $\Phi_\lambda$ is the radiant power of the exam lamp that is passed through the funduscope. In this case $N_{\Delta\lambda}$ for a 100 ms exposure, required to stay within the characteristic involuntary eye movement time interval, is estimated to be $$N_{\Delta\lambda} = 3.36 \times 10^4 R_\lambda$$

For the specific CCD cameras mentioned above, the electrons per pixel are $13.5 \times 10^3 R_\lambda$. For an 8% reflecting surface there would be 1080 electrons. This compares favorably with the total noise of about 4 electrons, indicating that we will be able to image the basic retina features. Additional improvement can be obtained by averaging several frames together, providing a $m^{1/2}$ decrease in noise where m is the number of frames averages.

To determine differences in the oxyhemoglobin and reduced oxyhemoglobin can be observed, the data in FIG. 11 is used. Based on these data a 0.5% change in the reflectance corresponds to about 54 electrons, 5 counts, which is four times larger than the noise. Note that the 0.5% change is also compatible with the shot noise limits that require a well depth of over 200,000 electrons. To measure 0.2% changes in reflectance, the lower values in FIG. 11, a well depth of 500,000 electrons is required, which is near the limits of sensitivity available in commercial cameras. Additional increases in signal can be obtained by increasing the illumination level, within eye safety (ANSI standards), which is feasible since the light is being narrow band filtered. A factor of two increase in illumination will make a 0.2% change in reflectance represent 40 electrons, a level that is still sufficiently above the noise to allow detection. Improvements can also be obtained by averaging several frames together, providing a $m^{1/2}$ decrease in noise where m is the number of frames averaged.

An assessment of the radiometrics indicates that, within the limits of the data used in the assessment, there is a high probability of being able to observe as little as 0.1% change in oxyhemoglobin saturation.

Measurement of changes in signals that are on the order of 1% are facilitated by a system that has a stable light source for interrogation, a stable (repeatable) CCD camera sensor, and an interrogating light signal (reflected from the retina) that is of sufficient magnitude.

Figure 3:
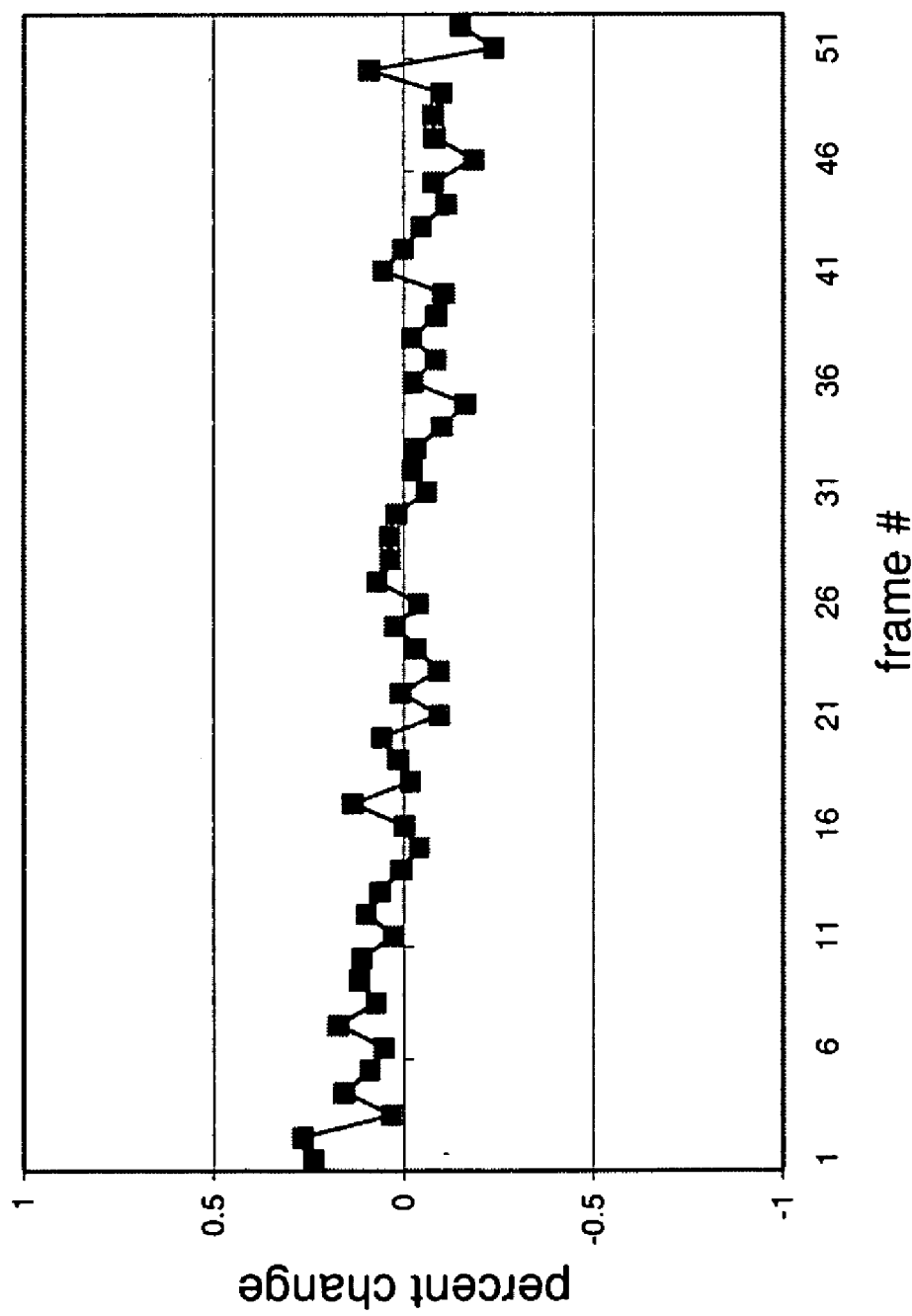
FIG. 3 depicts reflectance intensity for a 5% reflectance target.

In one embodiment, a research grade regulated power supply was used to stabilize the light source in the Canon camera to within 0.1%. Next, an experiment was conducted to measure the frame to frame stability of the OID-RF system. A sequence of 80 frames captured the light reflected from a NIST standard reflectance object. The object was an "artificial eye" designed for the sole purpose of calibrating fundus cameras. The reflectance was recorded over time (FIG. 3). The frame-to-frame changes in reflectance were on the order of only 0.1%. This met our requirements for measuring optical changes related to function from the human retina in the expected order of 1–5%.

In another embodiment, the liquid nitrogen cooled digital camera could be replaced with a thermo-electrically (TE) cooled camera. An alternative embodiment can use a 16-bit liquid nitrogen cooled camera. The thermoelectrically cooled camera can be smaller, will not require liquid nitrogen cooling, and will operate at a higher frame rate.

A TE camera can be compact and lightweight and require no operator intervention. The reduction in weight of the camera eliminates the need for a large camera support structure, further reducing the overall system size and weight and improving ease of alignment and operation. Thus, the TE camera can be supported by the mechanical coupling that attaches it to the Canon exit optics in much the same manner as a film camera. The frame-transfer aspect of the new camera allows for relatively high collection rates without the use of a mechanical shutter.

Image Processing

Figure 15:
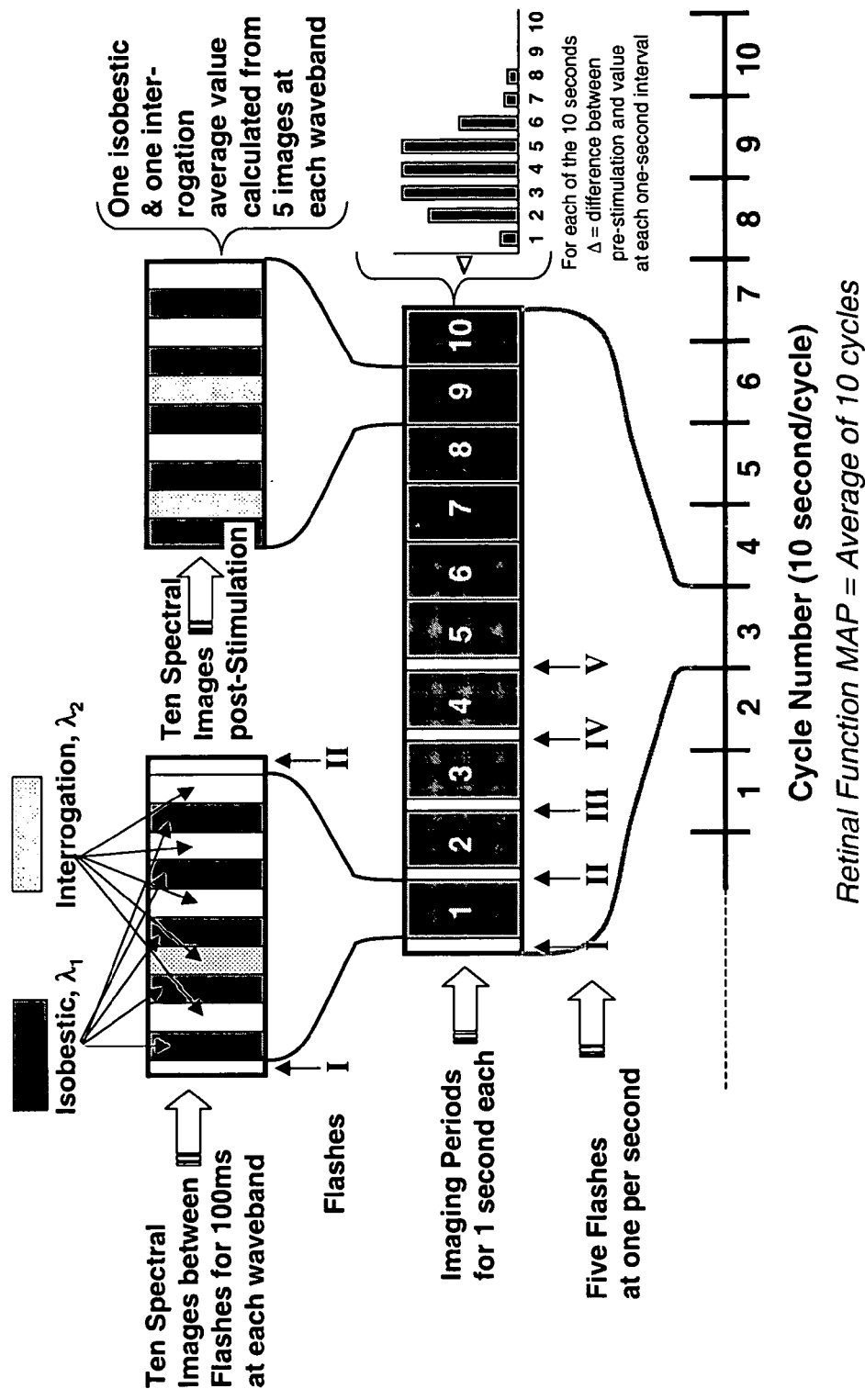
FIG. 15 depicts exemplary image collection and data processing.

In some embodiments of the invention, the stimulus and interrogation results in a two dimensional, 30 deg. field of view map of the retina. In the case of one embodiment, the following steps outline the image processing method for obtaining functional maps of the retina for each one-second period during stimulus and recovery cycle (see FIG. 15):

1. image frame-to-frame registration (alignment) using a software registration algorithm;
2. averaging of frames collected with isobestic wavelength interrogation light during each one second interval (5 frames) to reduce SNR. The same averaging of frames collected with active wavelength light during the same one second interval. These will be referred to as "averaged one-second frames;"
3. ratio (to remove frame-to-frame variations in illumination) of isobestic and active averaged one-second frames to yield "ratio frames" for each one second interval. Each ratio frame reflects an oxyhemoglobin saturation measurement during that interval;
4. averaging of all ratio frames in step 3 over the same time interval for all 10 cycles;
5. subtraction of the baseline ratio frame (the one-second ratio frame obtained immediately prior to stimulation) from those obtained during stimulation. These subtracted frames will reflect stimulus-evoked change in oxyhemoglobin saturation and hence, functional maps of the retina.

Functional maps obtained using the method disclosed above can be used to differentiate healthy from diseased areas of the retina. Functional maps obtained at one second intervals can be used to track time-dependent changes in retinal oxygen saturation resulting from retinal activation of neurons. Functional maps obtained at time points when the stimulus-evoked response is maximal are expected to correspond to visual field results.

Image Analysis

In one embodiment, video data can be collected at 4 frames per second for 13 seconds. A Windows-based image analysis system can be developed. Since there can be one or more eye saccades per second, the effects of eye movement were removed by registering individual frames in the video to a base frame. The image processing calculated statistics on individual video and combined videos, and provided data for plotting and analysis.

In one embodiment, the data acquisition system can be enhanced to provide immediate feedback of data quality at the time of collection. Immediately following the collection of each epoch, this improved system can register each frame of the epoch and display a chart showing the raw data for one or more specific regions on the retina. This chart can be encoded (with color and threshold bars) to indicate frames considered unacceptable. Examples of situations that can lead to a frame being excluded are blinks, excessive eye movements, and alignment artifacts such as crescent glares. The operator can either inspect the entire epoch by displaying each frame in succession as a video, or examine any individual frame by clicking at the corresponding location on the displayed graph. Such graphical interfaces are somewhat intuitive and very efficient to use, thus allowing for quick assessment of the data prior to proceeding with data collection. If, based upon the provided information, the operator decides that a given epoch is unacceptable, then the data can be reacquired. The new acquisition system can produce two sets of data; the original and the registered epochs.

In another embodiment, assessment of overall signal quality can be performed. At any point in the data collection, the operator can immediately produce a chart of cumulative signal strength based on the average of all previously collected epochs for one or more specific regions on the retina. This information can allow the operator to judge the need for additional epoch collection.

In yet other embodiment, the analysis software can be fully integrated into a functional graphical interface. In this embodiment, all functionality can be combined into a single software application. The analysis application can allow the user to select the desired data for analysis, then automatically perform any registration, averaging the epoch data, and finally producing standardized signal charts and maps for the various regions on the retina. Since the data acquisition software will now produce registered data in conjunction with data assessment, further registration during analysis will be unnecessary.

Method of Analysis of Retinal Images for Extraction of Functional Signal

In one embodiment, the post-collection processing of the functional signals involves first improvement of the signal to noise ratio by image registration, and image selection (identifying frames with artifacts from excessive eye movements, blinking, or abnormal reflections from the retina caused by camera misalignment or optical interference from a poor tear film, and deleting them from analysis). This step can make the difference in obtaining a good optical functional signal, because it is a software method that systematically identifies noisy camera recording frames and these can then by selectively deleted to improve the average signal from the frames that were not noisy.

In another embodiment, the method can employ derivative analysis. In this method, a time-segment before-the stimulus phase is used as a "control" segment of image frames which act as a baseline state and are compared to the image frames collected during the stimulus phase. By using a time segment of image frames just preceding the stimulus phase of image frames, any changes not due to the stimulus can be subtracted or divided out of the extracted signal. It is an improved method for removing changes in reflectance of the interrogating light that are not due to the stimulus itself and avoids non-stimulus associated artifacts from being extracted as part of the functional signal.

In other embodiments, analysis tools are used to more efficiently detect a stimulus associated signal and use software signal analysis methods such as principal component analysis and blind source separation.

Figure 17:
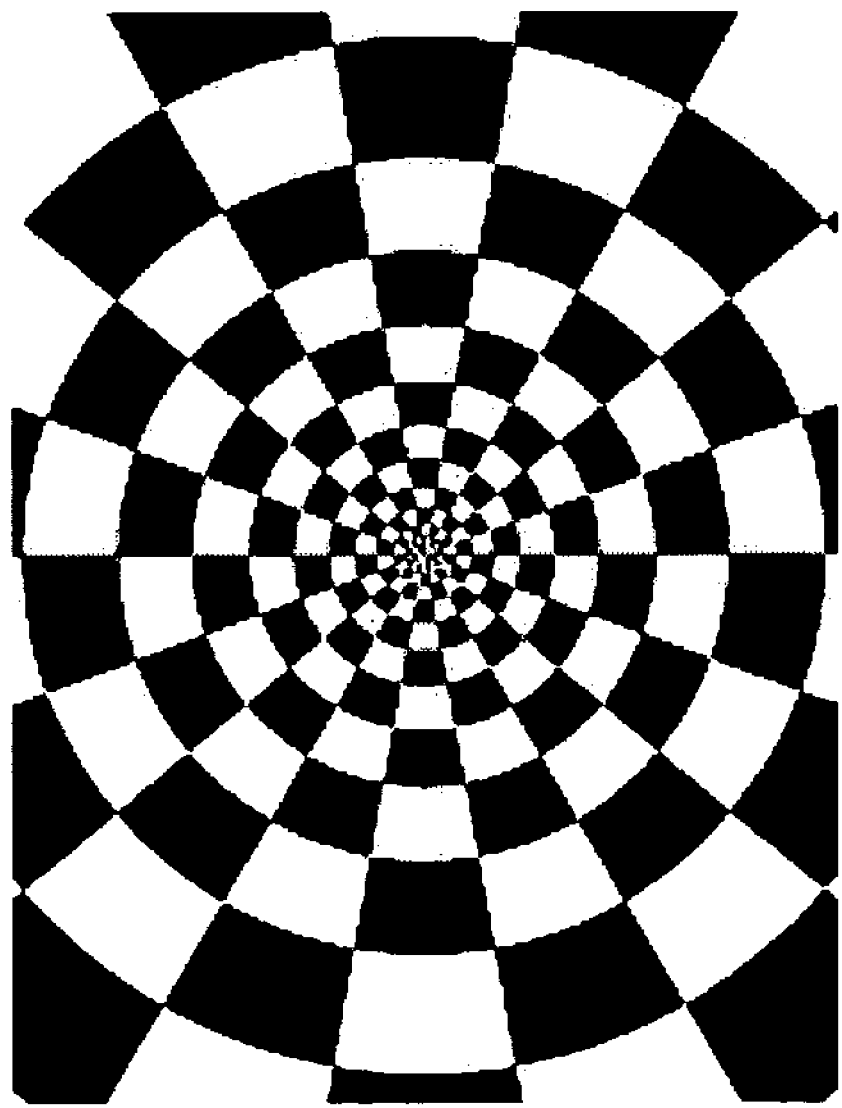
FIG. 17 depicts a patterned stimulus scaled with eccentricity and logarithmic distribution of photoreceptors.

Besides applying novel signal analysis methods, the present invention can also use the dynamics of the functional signal to probe the effects of disease and stimulus conditions. In one embodiment, the system can analyze a change in the functional signal by analyzing the decrease in reflectance caused by a stimulus (see FIGS. 17 and 18). In another embodiment, the system can analyze for increases in reflectance caused by a stimulus (see FIG. 19).

Figure 18:
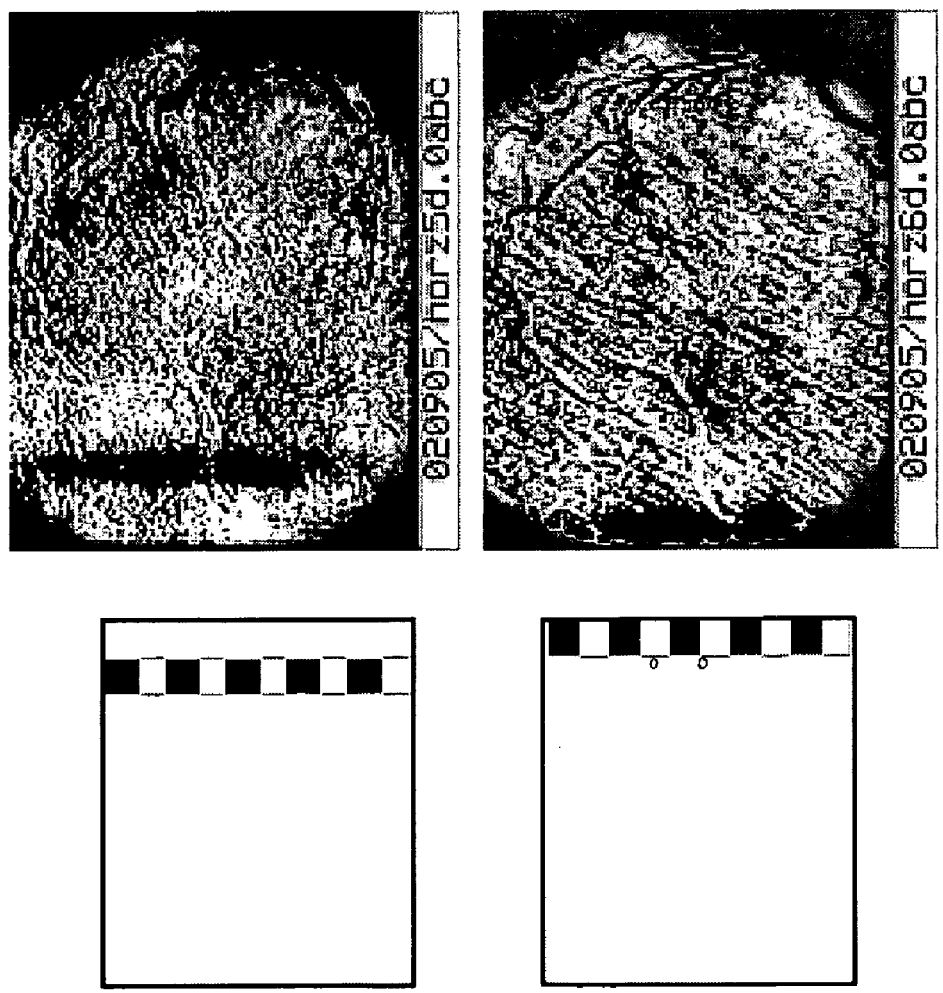
FIG. 18 depicts a functional image obtained from a cat's retina showing activation of an area of the retina.

FIG. 18 depicts an example of a functional image obtained from a cat's retina showing activation of an area of the retina (dark bar area) which corresponds to the location of where the horizontally located bar was seen during the stimulus phase. As the bar was moved further to the animals right field of view (lower figures), the vertical activation area appearing as a dark bar moves to the left of the center (foveal retinal area) of the field of view, which corresponds to the region of the retina where the stimulus bar was imaged.

Figure 19:
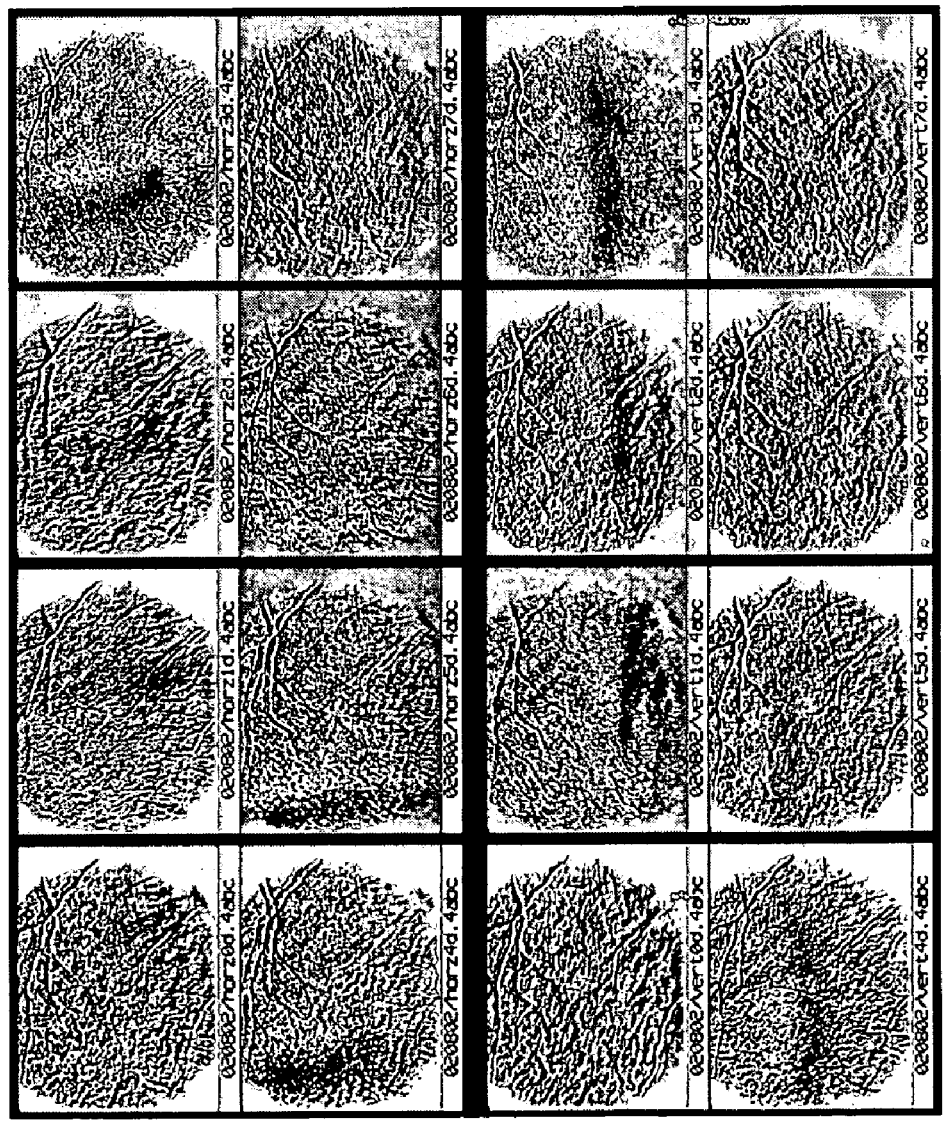
FIG. 19 depicts functional images of a cat's retina obtained from experiments illustrating the appearance of the functional activation.

FIG. 19 depicts functional images obtained from cat experiments showing the appearance of the functional activation of the portion of the retina where the bar was placed. In each panel, the functional image of the bar is located in the orientation and location that was changed, depending on the experimental condition. The top 8 panels are from experiments where the vertically oriented bar was moved to different horizontal locations across the retina. The bottom 8 panels are from experiments where a horizontally oriented stimulus bar was moved to different vertical locations. The functional activation area appears as a corresponding dark area in the image. The small lines seen represent the outlines of the superficial retinal blood vessels derived from the central retinal artery. This figure demonstrates the extraction of the functional image and the high correspondence between orientation and location of the stimulus and functional image in a normal cat eye.

Figure 20:
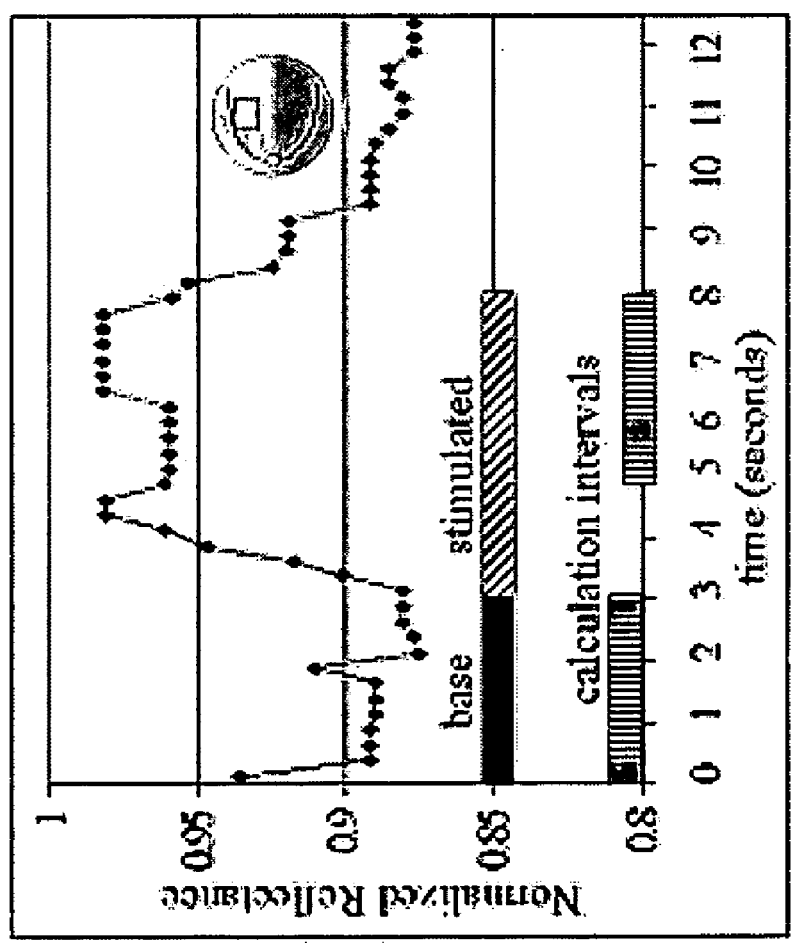
FIG. 20 depicts functional activation of a normal human retina.

FIG. 20 depicts an example of functional activation in the normal human retina. In this experiment, a visual stimulus with a pattern was placed on the superior half of the retina. The stimulus subtended almost the entire half of the retina within the field of view of the CCD sensor. The figure shows the increase in reflectance of the interrogating light during the activation stimulus phase. The small diagram shows the area of retina in the superior portion from which the line graph was made.

Experimental Design

The subject's eye was dilated with 1% tropicamide and 0.5% phenylephrine. The examination room was darkened, but the subjects were not fully dark adapted. A single data collection epoch consisted first of a baseline period (3 seconds), where no stimulus was presented, but interrogation light was used to collect the reference reflectance intensity. The baseline period was followed by a 5 second stimulation period, and then a 5 second recovery period. FIG. 4 illustrates a single epoch.

The camera was binned at 8×8 pixels to form a 162×167 image from a 45° diameter field of view (FOV). Thus, each pixel roughly represented a 0.20° or about 40 μm on the retina. A fixation cross was placed near the center of the subject-eye's field of view. This resulted in the fovea appearing near the center of the image and the optic disc on the right side of the image (for the imaging of the right eye). At a 4 Hz collection rate, each epoch started with approximately 12 frames of baseline data, followed by 20 frames of stimulus and 20 frames of recovery. Throughout the 13 seconds of data collection, the subject was asked not to blink. Frames with blinks or saccades or loss of fixation were deleted by the image processing software.

There were two stimulus pattern protocols presented to the subjects. FIG. 5 depicts the protocols. For each stimulus pattern, twenty to thirty epochs were collected. Each epoch was separated by a 10–20 s resting period where the subject could close his/her eyes, blink, and otherwise relax.

Figure 5B:
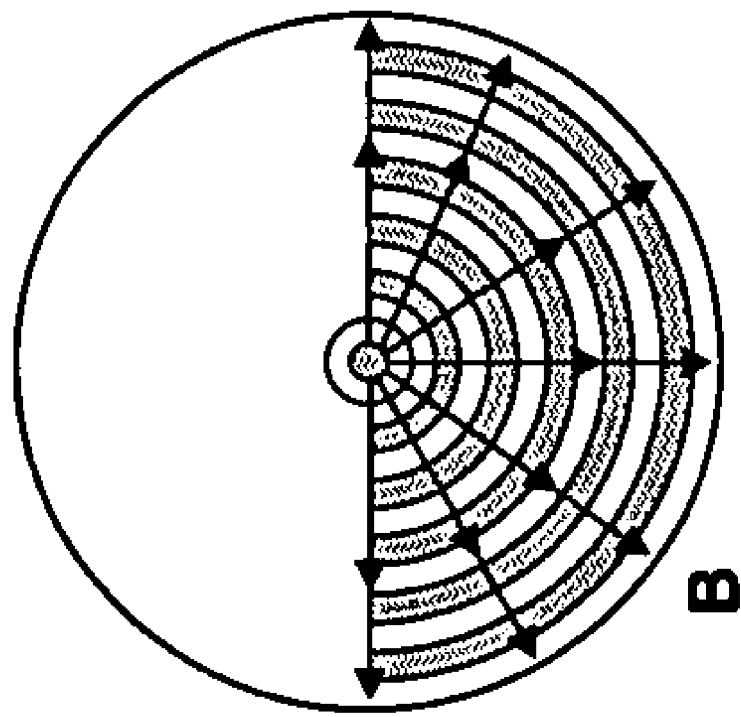
FIG. 5b depicts a stimulus pattern used in an alternate embodiment of the device.
Figure 5A:
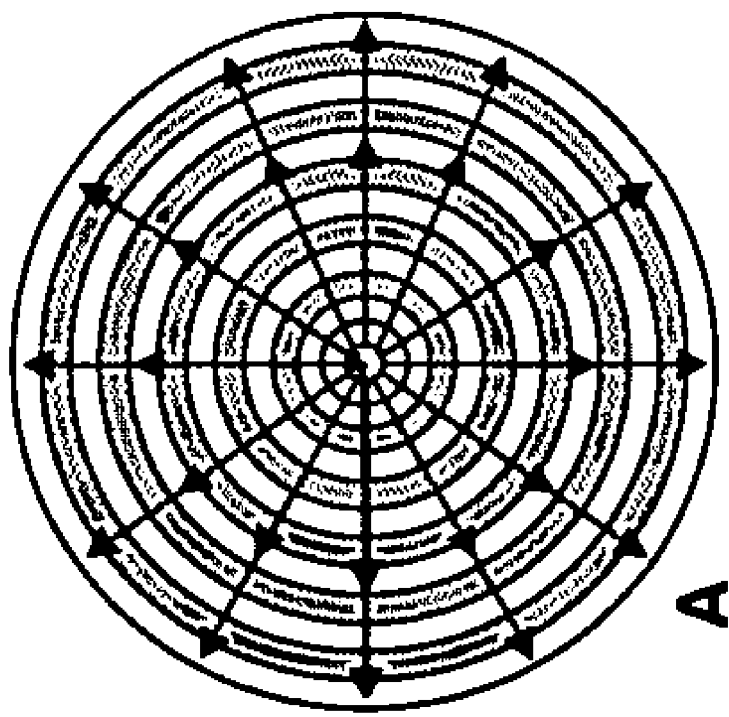
FIG. 5a depicts a stimulus pattern used in one embodiment of the device.

The pattern of FIG. 5a covered almost the entire 45 degree diameter field of view. The structure of this stimulus consisted of a circular pattern radiating from the center, which was marked with a fixation cross. The stimulus pattern of 5b was a hemispheric semi-circular pattern, also radiating from the center and could be displayed either superiorly or inferiorly.

In addition to the effort applied to the design of the OID-RF device to achieve the best possible signal to noise ratio (SNR), we also implemented a number of signal processing techniques to further improve our results. The data analysis procedure that is described below was developed and implemented to run on a standard desktop personal computer. A Pentium III (850 MHz) computer was found sufficient to process the data.

Figure 6:
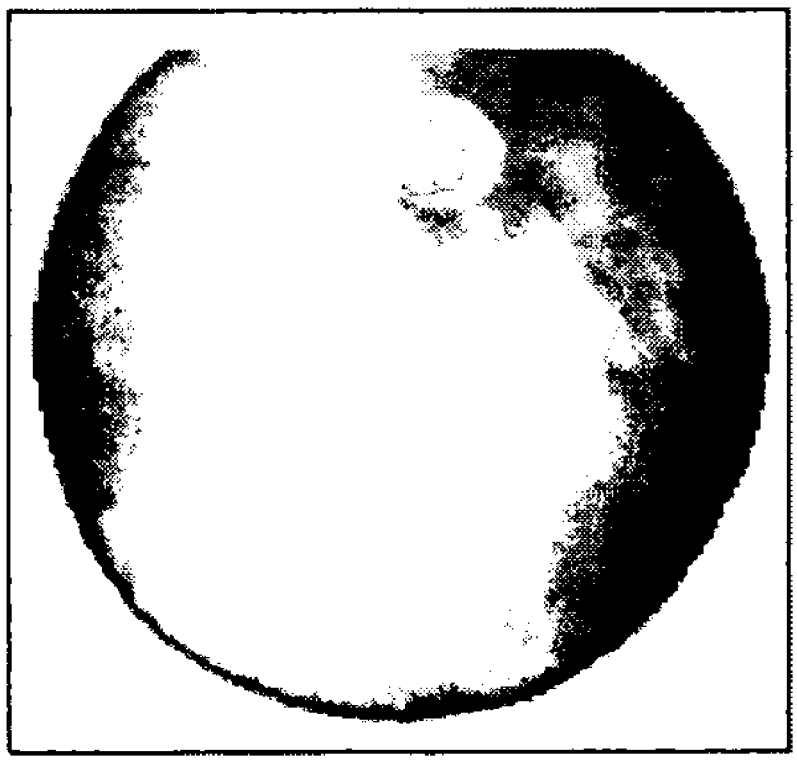
FIG. 6 depicts a typical image of interrogation light (700 nm).

A typical image sequence for a 13 second epoch consisted of 52 frames of data taken at 4 Hz. The pre-processing of the data started with the registration (alignment) of the individual frames. The location of the optic nerve, the most prominent and consistent feature in every image frame, was used as the basis for frame alignment. FIG. 6 shows a typical frame taken at 700 nm. The disc is the bright circular region on the right. For each epoch, each frame within the epoch was mapped onto a grid where the disc was always located at the same position. This alignment of frames enabled multi epoch averaging and frame-to-frame differencing The stimulus and interrogation resulted in a two dimensional, 45° diameter field of view map of retinal function. The following steps outline the image processing paradigm for obtaining time plots of the optical changes related to function. These time plots are shown for different locations on the retina and the optical signal is resolved for each one-second period during the baseline, stimulus, and recovery cycle (see FIG. 4).

The OID-RF instrument's image collection rate was determined by the digital camera that was being used. The Roper CCD camera collected 8×8 binned images at 4 Hz with 60 ms of integration time per frame. Image frame-to-frame registration (alignment) was performed automatically using the optic disc as the reference point, as was previously described.

Averaging to improve the signal to noise took place at two points in the process. First, the CCD camera was programmed to bin 8×8 pixels into a single readout value. This had the effect of removing some of the camera's random variations from electronic noise. The second averaging took place after the 162×167 binned image had been collected. Further averaging was performed by adding several epochs together where the same stimulus protocol had been used. Finally, spatial averaging to reduce the 162×167 to a 10×10 image further improved the signal to noise ratio.

Results

Our pretest estimates based on Beer's law indicated that the stimulus response from the retina could be as large as 10%, which was at least one order of magnitude greater than the minimum change in intensity that the instrument can detect above the noise fluctuations.

Figure 7:
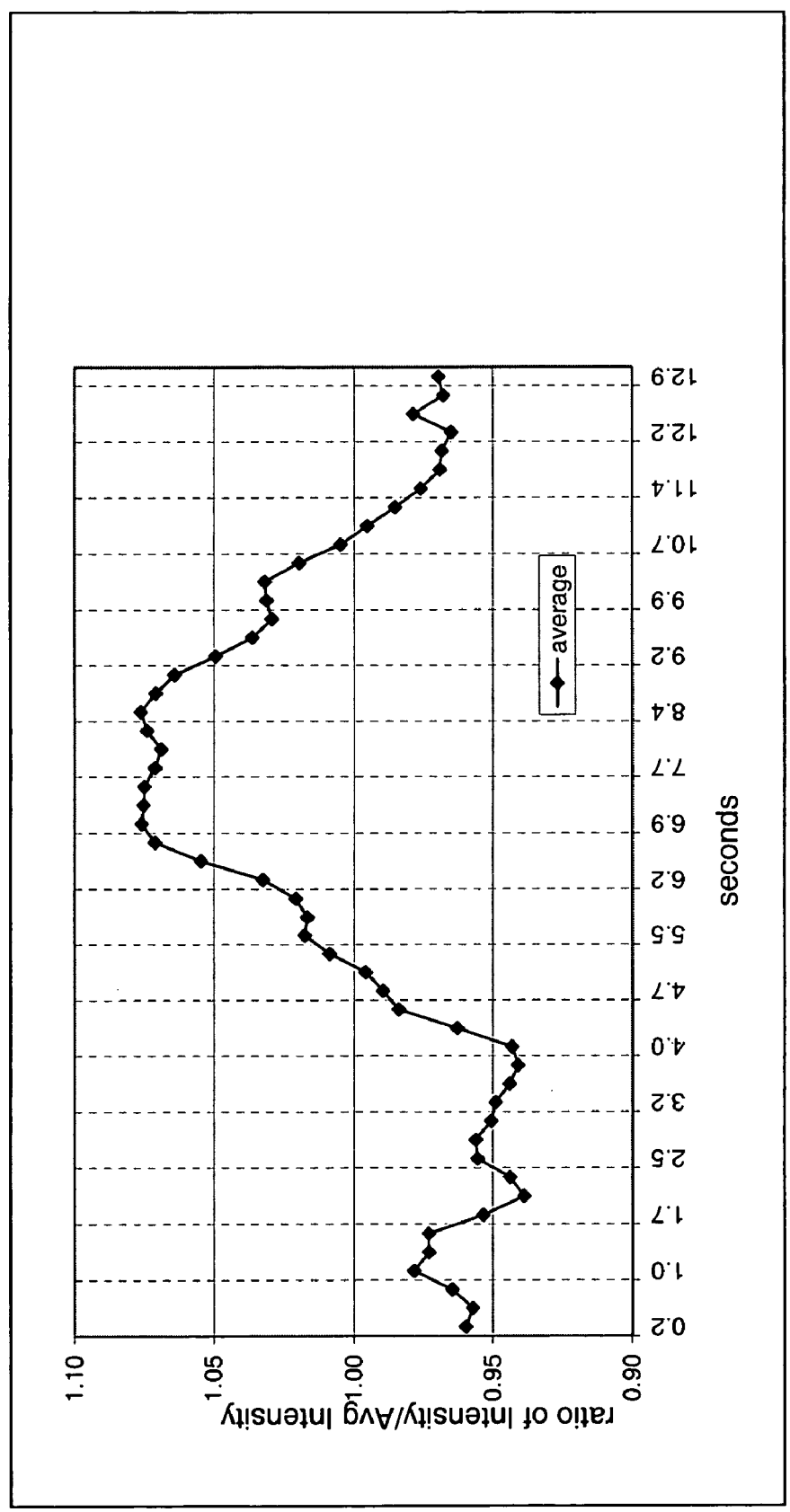
FIG. 7 depicts an exemplary reflected light intensity for a region centered on a macula.

Data for normal subjects M3 and M5, two representative cases, are presented. A patient (M7) with inferior hemiretinal damage caused by a branch retinal artery occlusion (BRAO) will also be briefly discussed. Subject M3 is a 40 year old Hispanic female. Subject M5 is a 56 year old anglo female. From our first experiment, FIG. 7 shows the results based on an average of 10 epochs where the reflected intensity for a 10° region centered on the macula was spatially integrated to produce one intensity value of the reflected interrogation light at each point in time. Stimulus (FIG. 5a), covering almost the entire field of view, was used. As noted above, the first three seconds were the pre-stimulus baseline data, followed by 5 seconds of stimulation, and 5 seconds of recovery. The purpose of the experiment was to determine whether a stimulus response signal could be measured for a normal subject.

One can see from FIG. 7 that within 1s after stimulus onset (at the 4 second point in time), the reflected intensity begins to increase steadily reaching a maximum of 12.5% above the baseline value, i.e. from 0.95 to 1.075. At 8.4s, almost immediately after the stimulus has been turned off, the intensity begins to decay, reaching a post stimulus value that is 3% above the initial baseline value. This profile is consistent with observations made by others of measuring the brain's visual cortex, e.g. Villringer (Villringer, A. and B. Chance, Non-invasive optical spectroscopy and imaging of human brain function. TINS, 1997. 20(10): p. 435–439.) This result is very encouraging, as it shows a stimulus-related optical signal and time course expected from an optical functional signal.

Figure 9B:
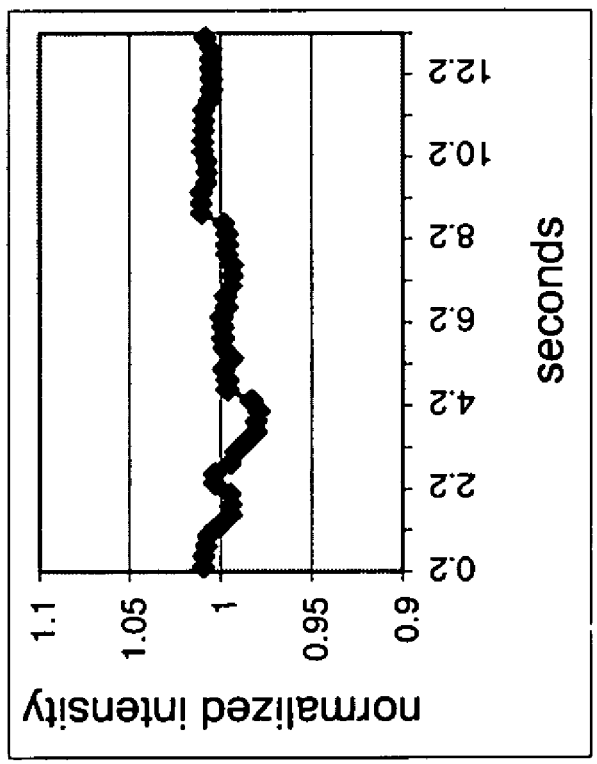
FIG. 9b depicts average reflected light intensity for inferior regions of a retina.
Figure 9A:
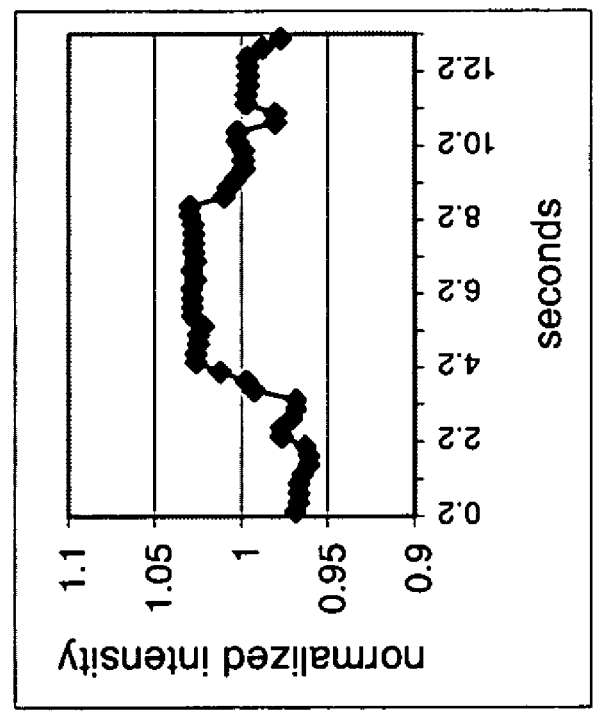
FIG. 9a depicts average reflected light intensity for superior regions of a retina.

In another experiment, Subject M5, another normal subject, was presented with stimulus (FIGS. 5a and 5b), where the inferior hemifield (superior retina) was stimulated and the inferior retina was not. FIGS. 9a and 9b show the spatially average reflected intensity over time for a region of about 8° in diameter in the inferior and superior regions of the retina, respectively. The two regions were about 3° vertically up or down from the fovea. These two spatially removed regions were selected to ensure there was no "crosstalk" near the boundary of the stimulus at the horizontal meridian. Note that when the presentation of a stimulus is in the inferior hemifield, the pattern is projected onto the superior hemisphere of the retina. This is caused by the inverting optics of the eye. The difference between the stimulated region, FIG. 9a, and the unstimulated region, FIG. 9b, is clear. The correlation between the two curves is −0.47, indicating that there is no similarity in the two time sequences. This result was also very encouraging as it demonstrated a regional difference in the optical functional signal collected at the same time between the stimulated and unstimulated areas of the retina. The examples in FIGS. 9a and 9b also demonstrate that internal ocular scatter dos not mask the adjacent retinal function signal.

Figure 10:
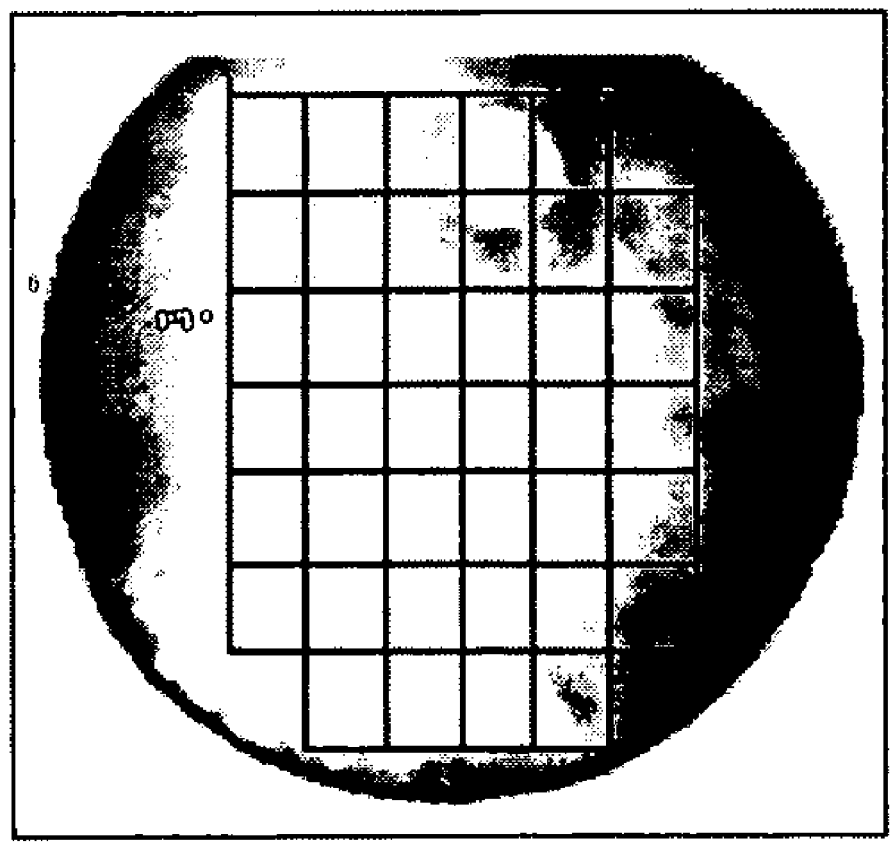
FIG. 10 depicts location of regions on an image frame of the device.

In FIGS. 7, 9a, and 9b, relatively large spatial regions were used to demonstrate the functional imaging of the retina. Since our ultimate goal is to present spatially resolved functional images, the next task involved dividing the retina into a regular grid of smaller regions and examining the signal for each region. FIG. 10 shows a grid that represents the regions created from spatially averaging 16×16 pixels. Each region has an extent of about 2.5°. Stimulus (FIG. 5b)

was used in this experiment to demonstrate spatial resolution of the optical functional signal. The subject was M5. The horizontal meridian along the center of the image (approximately the superior edge of the optic disc) marks the boundary between the stimulated superior hemiretina and the unstimulated inferior hemiretina.

The data are for a single epoch. Region 4,5 (fourth row and fifth column) was selected to represent a stimulated area. This region shows the characteristic waveform that was seen FIG. 7 for the full field stimulation consisting of increased reflectance after 4 second and slow decay after the stimulus ends (8 second mark). FIG. 8 shows the correlation coefficient between Region 4, 5 (row 4, column 5) and all the other regions. It is clear from FIG. 8 that the correlation is at a maximum in the superior hemisphere and is minimum in the inferior hemisphere.

There are a few exceptions where a region in the unstimulated hemisphere, (e.g. row 6, columns 2 through 5, as well as a few of the locations below it) showed strong correlation to the stimulated example, Region 4,5. This could indicate that there is a component of the response to the stimulated regions that is not entirely local, implicating some "sympathetic" response from the surrounding retinal circulation. This may provide important clues as to the source of the increase in reflectance of the optical signal and how the retinal circulation may react in response to local depletions of oxygen.

Finally, M7, one 69 year-old with an inferior branch retinal artery occlusion (superior visual field defect) was studied. His optical functional signal was very different in the normal area of the retina compared to the damaged area, where ganglion cells and axons had atrophied from the event which occurred 5 years earlier. The differences observed between the normal and damaged area of retina demonstrated proof of concept that the technique is capable of detecting non-functioning areas of the inner retina. The "inverted" time plot of the functional signal in the normal area of the retina in this patient is interesting, and could represent a variation in response changes in oxygen consumption.

From the data presented here, it is believed that the technique presented for detecting such functional activation of the retina is possible and practical. The results indicate that a measurable change in the optical reflection of near infrared 700 nm light (separated from the 530 nm wavelength of the visual stimulus) can be observed as a result of functional activation of the retina. This forms the basis of an instrument and method that provides functional imaging of the retina, and in so doing yields new, objective information on retinal function in response to visual stimulation in normal and diseased states.

Although preferred embodiments of the invention has been disclosed in the forgoing specification, it is understood by those skilled in the art that many modifications and other embodiments of the invention will come to mind to which the invention pertains, having the benefit of the teaching presented in the foregoing description. Accordingly, it is understood that the invention is not limited to specific embodiments disclosed herein, and that many modifications and other embodiments of the invention are intended to be included in the scope hereof. Moreover, although specific terms are employed herein, they are used in the generic and descriptive sense only, and are not intended to limit the scope of the invention.

We claim:

1. An apparatus for the functional imaging of a retina comprising:
   a. a stimulation source positioned with respect to the retina;
   b. a retinal interrogator constructed and arranged to emit light in the direction of the retina and along an optical path;
   c. a detector constructed and arranged to detect the light emitted from the retinal interrogator and reflected from the retina;
   d. wherein the retinal interrogator is constructed and arranged to emit light in a plurality of wavelengths and positioned to transmit light through a and sclera; and
   e. a computer for analyzing the light detected by the detector, the light comprising a retinal image frame, and extracting a signal that corresponds to stimulus-evoked activity of a specific class of retinal cells thereby determining a relationship of a baseline response to the stimulation source.

2. The apparatus of claim 1, wherein the stimulation source is constructed and arranged to be selectively disabled.

3. The apparatus of claim 2, wherein the retinal interrogator is mounted on a contact lens.

4. The apparatus of claim 1, wherein the retinal interrogator is constructed and arranged to transmit light through a lower eyelid.

5. The apparatus of claim 1, wherein the retinal interrogator is constructed and arranged to transmit light through an inferior orbital area.

6. The apparatus of claim 1, wherein the retinal interrogator is constructed and arranged to emit light in a range of near infrared wavelengths.

7. The apparatus of claim 1, wherein the retinal interrogator is constructed and arranged to emit light in a range of infrared wavelengths.

8. The apparatus of claim 1, wherein the retinal interrogator comprises at least one light emitting diode.

9. The apparatus of claim 1, wherein the detector comprises at least one CCD sensor.

10. The apparatus of claim 1, further comprising an Allen dot placed in the optical path wherein the Allen dot masks optic nerve head reflection.

11. The apparatus of claim 1, wherein the stimulation source activates a specific class of retinal cells wherein differences in stimulus wavelength, spatial pattern, spatial frequency, temporal pattern, temporal frequency, eccentricity, contrast, intensity, motion, and properties of adaptation facilitate activation.

12. The apparatus of claim 11, wherein the retinal cells activated are selected based an attribute selected from the group consisting of:
   functional type;
   layer;
   location;
   functional type and layer;
   functional type and location; and
   layer and location.

13. The apparatus of claim 1, wherein the stimulation source selectively stimulates a layer of the retina.

14. The apparatus of claim 1, wherein the stimulation source differentially stimulates two different sets of retinal layers wherein activity of one of the sets of retinal layers is isolated.

15. A method for stimulating a functional signal in a retina comprising the steps of:
   a. recording a baseline retinal response wherein the recording comprises transmitting light through a sclera;
   b. applying a stimulus to the retina during a stimulus phase;
   c. recording a retinal response during the stimulus phase wherein the recording comprises transmitting light through a sclera; and
   d. computing a relationship of the baseline response to the stimulus response by analyzing a captured retinal image frame, the captured retinal image frame comprising the recorded stimulus response, and extracting a signal that corresponds to stimulus-evoked activity of a specific class of retinal cells.

16. The method of claim 15, further including the step of applying a stimulus to the retina while recording the baseline retinal response.

17. The method of claim 16, wherein the step of recording the baseline retinal response comprises the application of a diffuse luminant stimulus to the retina.

18. The method of claim 15, wherein the applied stimulus comprises a selectable spatial frequency.

19. The method of claim 15, wherein the applied stimulus comprises a visually perceptible pattern.

20. The method of claim 15, wherein the applied stimulus is applied with at least one LCD.

21. The method of claim 20, wherein the at least one LCD is positioned with respect to the retina along an optical path of a fundus camera.

22. The method of claim 15, wherein the stimulus applied activates a specific class of retinal cells wherein differences in stimulus wavelength, spatial pattern and frequency, temporal pattern and frequency, eccentricity, contrast, intensity, motion, and properties of adaptation facilitate activation.

23. The method of claim 22, wherein the retinal cells activated are selected based on an attribute selected from the group consisting of:
   functional type;
   layer;
   location;
   functional type and layer;
   functional type and location; and
   layer and location.

24. The method of claim 15, wherein the stimulus applied selectively stimulates a layer of the retina.

25. The method of claim 15, wherein the stimulus applied differentially stimulates two different sets of retinal layers wherein activity of one of the sets of retinal layers is isolated.

26. The method of claim 15 wherein the step of analyzing further comprises:
   registering the retinal image frames.

27. The method of claim 15 wherein the step of analyzing further comprises:
   grouping and averaging the retinal image frames.

28. The method of claim 15 wherein the step of analyzing further comprises:
   removing variations in illumination in the retinal image frames.

29. The method of claim 15 wherein the step of analyzing further comprises:
   correcting for a baseline frame in the retinal image frames.

30. The method of claim 15 wherein the step of extracting a stimulus response provides immediate feedback of data quality at the time of collection.

31. A system for the functional imaging of a retina, comprising:
   a. a means for stimulating the retina;
   b. a means for interrogating a retinal response to the stimulation means wherein the means for interrogating the retina comprises a means for illuminating the retina via transcleral illumination;
   c. a means for detecting a reflection of light from the retina resultant from the interrogating means; and
   d. a means for analyzing the light detected by the detector, the light comprising a retinal image frame, and extracting a signal that corresponds to stimulus-evoked activity of a specific class of retinal cells thereby determining a relationship of a baseline response to the stimulation source.

32. The system of claim 31, wherein the means for stimulating the retina comprises a means for emitting light.

33. The system of claim 32, wherein the means for emitting light comprises at least one LCD.

34. The system of claim 31, wherein the means for interrogating the retina comprises a means for emitting light in at least one near infrared wavelength.

35. The system of claim 31, wherein the means for interrogating the retina comprises a means for emitting light in at least one infrared wavelength.

36. The system of claim 31, wherein the means for interrogating the retina comprises an emitter constructed and arranged to emit light at a wavelength in the range of 700 nm to 900 nm.

37. The system of claim 31, wherein the means for interrogating the retina comprises at least one LED.

38. The system of claim 31, wherein the means for interrogating the retina comprises a halogen light source.

39. The system of claim 31, wherein the means for interrogating the retina comprises a tungsten light source.

40. The system of claim 31, wherein the means for detecting the reflection comprises a CCD.

41. The system of claim 31, wherein the means for stimulating activates a specific class of retinal cells wherein differences in stimulus wavelength, spatial pattern and frequency, temporal pattern and frequency, eccentricity, contrast, intensity, motion, and properties of adaptation facilitate activation.

42. The system of claim 41, wherein the retinal cells activated are selected based on an attribute selected from the group consisting of:
   functional type;
   layer;
   location;
   functional type and layer;
   functional type and location; and
   layer and location.

43. The system of claim 31, wherein the means for stimulating selectively stimulates a layer of the retina.

44. The system of claim 31, wherein the means for stimulating differentially stimulates two different sets of retinal layers wherein activity of one of the sets of retinal layers is isolated.

* * * * *